United States Patent
Coenen et al.

(10) Patent No.: US 8,361,049 B2
(45) Date of Patent: Jan. 29, 2013

(54) BOXER SHORTS AND PROCESS OF MAKING BOXER SHORTS WITH EXPANDABLE MATERIAL

(75) Inventors: Joseph Daniel Coenen, Kaukauna, WI (US); Robert Lee Popp, Hortonville, WI (US); Heather Schenck Mortell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1437 days.

(21) Appl. No.: 10/954,989

(22) Filed: Sep. 30, 2004

(65) Prior Publication Data
US 2005/0120466 A1 Jun. 9, 2005

Related U.S. Application Data

(63) Continuation-in-part of application No. 10/314,915, filed on Dec. 9, 2002, now abandoned.

(51) Int. Cl.
*A61F 13/15* (2006.01)
(52) U.S. Cl. ...................... 604/396; 604/394
(58) Field of Classification Search .............. 604/358, 604/385.01, 385.14, 385.27, 393–397; 2/400–408
See application file for complete search history.

(56) References Cited

U.S. PATENT DOCUMENTS

| | | |
|---|---|---|
| 478,281 A | 7/1892 | Hamilton et al. |
| 1,577,409 A | 3/1926 | Rand |
| 1,664,298 A | 3/1928 | Katz |
| 1,971,558 A | 8/1934 | Goodman |
| 2,030,306 A | 2/1936 | Lain |
| 2,032,982 A | 3/1936 | Gerstman |
| 2,088,302 A | 7/1937 | McKeever |
| 2,116,822 A | 5/1938 | Berger |
| 2,131,808 A | 10/1938 | Joa |
| 2,242,526 A | 5/1941 | Kneibler |
| 2,252,019 A | 8/1941 | Meinecke et al. |
| 2,319,138 A | 5/1943 | Kneibler |
| 2,391,641 A | 12/1945 | O'Hern |
| 2,435,945 A | 2/1948 | Redmond |
| 2,450,789 A | 10/1948 | Frieman |
| 2,522,510 A | 9/1950 | Fridolph |
| 2,538,596 A | 1/1951 | Sheridan |
| 2,675,806 A | 1/1954 | Bram |
| 2,711,735 A | 6/1955 | Sabo |
| 2,838,047 A | 6/1958 | Sidnell |

(Continued)

FOREIGN PATENT DOCUMENTS

AT 168478 B 6/1951
CA 2356510 A1 2/2003

(Continued)

OTHER PUBLICATIONS

Printed materials (3 pages) showing pull-on diapers disclosed at a trade show Apr. 27-29, 2004 in Miami Beach, Florida, U.S.A.

(Continued)

*Primary Examiner* — Michele M Kidwell
(74) *Attorney, Agent, or Firm* — Armstrong Teasdale LLP

(57) ABSTRACT

A boxer-style pant and a method of making a boxer-style pant having side seams and hanging legs. Expandable material is used to provide a conforming fit and to expedite high-speed manufacture. The pant is made from a web and includes a garment shell having a front region, a back region, and a crotch region positioned between the front and back regions. The side seams connect the front region to the back region. The garment shell may be essentially composed of an expandable material that is selectively expanded in certain areas of the garment, and/or an expandable material may be attached to the garment shell in the crotch region and/or in the back region.

34 Claims, 14 Drawing Sheets

U.S. PATENT DOCUMENTS

| | | |
|---|---|---|
| 2,842,129 A | 7/1958 | Ernstorff |
| 2,859,752 A | 11/1958 | Haber |
| 3,245,407 A | 4/1966 | Mason |
| 3,338,992 A | 8/1967 | Kinney |
| 3,341,394 A | 9/1967 | Kinney |
| 3,418,660 A | 12/1968 | Shumate |
| 3,502,538 A | 3/1970 | Petersen |
| 3,502,763 A | 3/1970 | Hartmann |
| 3,542,615 A | 11/1970 | Dobo et al. |
| 3,611,443 A | 10/1971 | Braun |
| 3,648,699 A | 3/1972 | Anderson et al. |
| 3,678,516 A | 7/1972 | Backer |
| 3,692,618 A | 9/1972 | Dorschner et al. |
| 3,714,946 A | 2/1973 | Rudes |
| 3,739,398 A | 6/1973 | Sarmiento |
| 3,802,817 A | 4/1974 | Matsuki et al. |
| 3,806,007 A | 4/1974 | Grantham |
| 3,844,282 A | 10/1974 | King |
| 3,859,667 A | 1/1975 | Roy |
| 3,869,999 A | 3/1975 | Richter |
| 3,920,237 A | 11/1975 | Grantham |
| 4,059,257 A | 11/1977 | Grantham |
| 4,081,301 A | 3/1978 | Buell |
| 4,100,324 A | 7/1978 | Anderson et al. |
| 4,106,125 A | 8/1978 | Palumbo |
| 4,114,621 A | 9/1978 | Mims, Jr. |
| 4,116,892 A | 9/1978 | Schwarz |
| 4,145,763 A | 3/1979 | Abrams et al. |
| 4,223,059 A | 9/1980 | Schwarz |
| 4,227,952 A | 10/1980 | Sabee |
| 4,280,230 A | 7/1981 | LaFleur |
| 4,284,454 A | 8/1981 | Joa |
| 4,285,100 A | 8/1981 | Schwarz |
| 4,300,241 A | 11/1981 | Shaull |
| 4,310,929 A | 1/1982 | Finlay |
| 4,327,448 A | 5/1982 | Lunt |
| 4,338,939 A | 7/1982 | Daville |
| 4,340,563 A | 7/1982 | Appel et al. |
| 4,368,565 A | 1/1983 | Schwarz |
| 4,392,259 A | 7/1983 | Bredo |
| 4,397,704 A | 8/1983 | Frick |
| 4,417,938 A | 11/1983 | Sigl |
| 4,449,254 A | 5/1984 | Fogg |
| 4,543,141 A | 9/1985 | Bradley et al. |
| 4,555,245 A | 11/1985 | Armbruster |
| 4,597,110 A | 7/1986 | Smith, Sr. et al. |
| 4,608,115 A | 8/1986 | Schroth et al. |
| 4,644,945 A | 2/1987 | Thorner |
| 4,646,362 A | 3/1987 | Heran et al. |
| 4,650,530 A | 3/1987 | Mahoney et al. |
| 4,655,760 A | 4/1987 | Morman et al. |
| 4,663,106 A | 5/1987 | Pomplun et al. |
| 4,663,220 A | 5/1987 | Wisneski et al. |
| 4,665,306 A | 5/1987 | Roland et al. |
| 4,671,793 A | 6/1987 | Hults et al. |
| 4,675,918 A | 6/1987 | O'Brien |
| 4,704,116 A | 11/1987 | Enloe |
| 4,745,636 A | 5/1988 | Lunt |
| 4,771,483 A | 9/1988 | Hooreman et al. |
| 4,786,346 A | 11/1988 | Ales et al. |
| 4,805,243 A | 2/1989 | Gibbens et al. |
| 4,816,094 A | 3/1989 | Pomplun et al. |
| 4,835,795 A | 6/1989 | Lonon |
| 4,847,134 A | 7/1989 | Fahrenkrug et al. |
| 4,870,958 A | 10/1989 | Webster |
| 4,872,221 A | 10/1989 | Stone, III |
| 4,875,240 A | 10/1989 | Barrett |
| 4,883,549 A | 11/1989 | Frost et al. |
| 4,892,536 A | 1/1990 | DesMarais et al. |
| 4,895,568 A | 1/1990 | Enloe |
| 4,935,021 A | 6/1990 | Huffman et al. |
| 4,946,539 A | 8/1990 | Ales et al. |
| 4,955,880 A | 9/1990 | Rodriquez |
| 4,964,860 A | 10/1990 | Gipson et al. |
| D315,050 S | 3/1991 | Bush et al. |
| 5,014,364 A | 5/1991 | Orr |
| 5,022,240 A | 6/1991 | Peleg |
| 5,046,272 A | 9/1991 | Vogt et al. |
| 5,052,058 A | 10/1991 | Mueller |
| 5,067,178 A | 11/1991 | Katchka |
| 5,087,253 A | 2/1992 | Cooper |
| 5,103,505 A | 4/1992 | Llorens |
| 5,135,522 A | 8/1992 | Fahrenkrug et al. |
| 5,147,487 A | 9/1992 | Nomura et al. |
| 5,171,388 A | 12/1992 | Hoffman et al. |
| 5,187,817 A | 2/1993 | Zolner |
| 5,210,882 A | 5/1993 | Moretz et al. |
| 5,217,782 A | 6/1993 | Moretz et al. |
| 5,226,992 A | 7/1993 | Morman |
| D341,243 S | 11/1993 | Costella et al. |
| 5,297,296 A | 3/1994 | Moretz et al. |
| 5,303,424 A | 4/1994 | Cromartie |
| 5,306,536 A | 4/1994 | Moretz et al. |
| 5,315,716 A | 5/1994 | Baum |
| 5,315,717 A | 5/1994 | Moretz et al. |
| 5,370,634 A | 12/1994 | Ando et al. |
| 5,379,462 A | 1/1995 | Morgan et al. |
| 5,382,246 A | 1/1995 | Kawano |
| 5,435,014 A | 7/1995 | Moretz et al. |
| 5,445,628 A | 8/1995 | Gipson et al. |
| 5,500,063 A | 3/1996 | Jessup |
| 5,545,158 A | 8/1996 | Jessup |
| 5,549,593 A | 8/1996 | Ygge et al. |
| 5,554,149 A | 9/1996 | O'Donnell |
| 5,556,504 A | 9/1996 | Rajala et al. |
| 5,566,392 A | 10/1996 | Dzelzkains |
| D377,557 S | 1/1997 | Jagger |
| 5,649,913 A | 7/1997 | Cohen |
| D382,386 S | 8/1997 | Malone |
| 5,669,902 A | 9/1997 | Sivilich |
| 5,669,996 A | 9/1997 | Jessup |
| 5,690,626 A | 11/1997 | Suzuki et al. |
| 5,690,627 A | 11/1997 | Clear et al. |
| 5,704,071 A | 1/1998 | Barclay et al. |
| 5,716,478 A | 2/1998 | Boothe et al. |
| 5,718,003 A | 2/1998 | Gwinn |
| 5,733,401 A | 3/1998 | Linman et al. |
| 5,746,730 A | 5/1998 | Suzuki et al. |
| 5,755,902 A | 5/1998 | Reynolds |
| 5,759,340 A | 6/1998 | Boothe et al. |
| 5,790,983 A | 8/1998 | Rosch et al. |
| 5,827,260 A | 10/1998 | Suzuki et al. |
| 5,853,405 A | 12/1998 | Suprise |
| 5,876,394 A | 3/1999 | Rosch et al. |
| 5,891,122 A | 4/1999 | Coates |
| D408,964 S | 5/1999 | Hernandez |
| 5,906,604 A | 5/1999 | Rönnberg et al. |
| 5,906,879 A | 5/1999 | Huntoon et al. |
| 5,907,872 A | 6/1999 | Alberts et al. |
| 5,921,974 A | 7/1999 | Kikuchi |
| 5,953,754 A | 9/1999 | Rosch et al. |
| 5,956,774 A | 9/1999 | Mackley |
| 5,978,971 A | 11/1999 | Wald |
| D417,940 S | 12/1999 | Coates et al. |
| 6,009,558 A | 1/2000 | Rosch et al. |
| 6,010,586 A | 1/2000 | Suprise |
| 6,018,822 A | 2/2000 | Hernandez |
| 6,022,443 A | 2/2000 | Rajala et al. |
| 6,105,171 A | 8/2000 | Niedermeyer |
| 6,142,983 A | 11/2000 | Suprise et al. |
| 6,145,132 A | 11/2000 | Towner |
| 6,149,637 A | 11/2000 | Allen et al. |
| 6,149,755 A | 11/2000 | McNichols et al. |
| 6,168,585 B1 | 1/2001 | Cesco-Cancian |
| 6,174,303 B1 | 1/2001 | Suprise et al. |
| 6,192,521 B1 | 2/2001 | Alberts et al. |
| 6,205,592 B1 | 3/2001 | Gouws |
| 6,248,097 B1 | 6/2001 | Beitz et al. |
| 6,287,169 B1 | 9/2001 | Willms et al. |
| 6,289,519 B1 | 9/2001 | Murakami et al. |
| 6,293,934 B1 | 9/2001 | Kumasaka |
| 6,293,936 B1 | 9/2001 | Otsubo |
| 6,293,937 B2 | 9/2001 | Matsushita et al. |
| 6,308,339 B1 | 10/2001 | Murakami et al. |
| 6,312,420 B1 | 11/2001 | Sasaki et al. |
| 6,319,347 B1 | 11/2001 | Rajala et al. |
| 6,342,050 B1 | 1/2002 | Rönnberg et al. |

| | | | | | |
|---|---|---|---|---|---|
| 6,368,312 B1 | 4/2002 | Otsubo | GB | 307652 | 3/1929 |
| D456,995 S | 5/2002 | Baker | GB | 571098 | 8/1945 |
| 6,463,591 B1 | 10/2002 | Toratani | GB | 620555 | 3/1949 |
| 6,475,201 B2 | 11/2002 | Saito et al. | GB | 701081 | 12/1953 |
| 6,513,221 B2 | 2/2003 | Vogt et al. | GB | 1342022 | 12/1973 |
| 6,516,473 B2 | 2/2003 | Saito | GB | 2069820 | 9/1981 |
| 6,539,554 B1 | 4/2003 | Portela | GB | 2112268 | 7/1983 |
| 6,560,786 B2 | 5/2003 | Lipton | GB | 2196525 | 5/1988 |
| 6,562,167 B2 | 5/2003 | Coenen et al. | GB | 2 208 263 | 3/1989 |
| 6,565,691 B2 | 5/2003 | Tomsovic et al. | GB | 2269978 | 3/1994 |
| 6,585,840 B2 | 7/2003 | Rabe et al. | GB | 2269998 | 3/1994 |
| 6,596,113 B2 | 7/2003 | Csida et al. | GB | 2269999 | 3/1994 |
| 6,610,901 B2 | 8/2003 | McMahon-Ayerst et al. | GB | 2327859 | 2/1999 |
| 6,626,883 B2 | 9/2003 | Wada et al. | JP | 04-242643 | 8/1992 |
| 6,666,851 B2 | 12/2003 | Otsubo et al. | JP | 2000 093462 | 4/2000 |
| 6,723,034 B2 | 4/2004 | Durrance et al. | JP | 2000 355801 | 12/2000 |
| 6,807,685 B1 | 10/2004 | Hasegawa et al. | JP | 2001 172801 | 6/2001 |
| 2001/0014798 A1 | 8/2001 | Fernfors | JP | 2001 172802 | 6/2001 |
| 2001/0044614 A1 | 11/2001 | Damay et al. | JP | 3177341 | 6/2001 |
| 2002/0000291 A1 | 1/2002 | Coenen et al. | JP | 2001 204762 | 7/2001 |
| 2002/0002021 A1 | 1/2002 | May et al. | JP | 2001 204764 | 7/2001 |
| 2002/0002358 A1 | 1/2002 | Durrance et al. | JP | 2001 204765 | 7/2001 |
| 2002/0009940 A1 | 1/2002 | May et al. | JP | 3182069 | 7/2001 |
| 2002/0084017 A1 | 7/2002 | Rabe et al. | JP | 2001 207301 | 8/2001 |
| 2002/0087137 A1 | 7/2002 | Christoffel et al. | JP | 2001 224615 | 8/2001 |
| 2002/0099345 A1 | 7/2002 | Saito et al. | JP | 2001 238909 | 9/2001 |
| 2003/0109842 A1 | 6/2003 | Louis et al. | JP | 2001 245929 | 9/2001 |
| 2003/0115660 A1 | 6/2003 | Hopkins | JP | 2001 248002 | 9/2001 |
| 2004/0098791 A1 | 5/2004 | Faulks | JP | 2001 254202 | 9/2001 |
| 2004/0102746 A1 | 5/2004 | Mortell et al. | JP | 2001 262402 | 9/2001 |
| 2004/0107481 A1 | 6/2004 | Mortell et al. | JP | 3205643 | 9/2001 |
| 2004/0116881 A1 | 6/2004 | Nordness et al. | JP | 3205690 | 9/2001 |
| | | | JP | 3208258 | 9/2001 |

FOREIGN PATENT DOCUMENTS

| | | |
|---|---|---|
| JP | 2001 299813 | 10/2001 |
| DE | 435 579 | 2/1927 |
| JP | 3221601 | 10/2001 |
| DE | 809 844 | 8/1951 |
| JP | 2001 309946 | 11/2001 |
| DE | 839 244 | 5/1952 |
| JP | 2001 333932 | 12/2001 |
| DE | 101 44 255 | 2/2003 |
| JP | 2002 095700 | 4/2002 |
| EP | 0 217 032 | 4/1987 |
| JP | 2002-320641 | 11/2002 |
| EP | 0 585 766 | 3/1994 |
| JP | 2004 159949 | 6/2004 |
| EP | 0 717 971 | 6/1996 |
| WO | WO 95/16421 | 6/1995 |
| EP | 0 763 353 | 3/1997 |
| WO | WO 95/18589 | 7/1995 |
| EP | 0 549 988 | 6/1998 |
| WO | WO 96/03950 | 2/1996 |
| EP | 0 904 758 | 3/1999 |
| WO | WO 97/02797 | 1/1997 |
| EP | 0 911 006 | 4/1999 |
| WO | WO 99/33421 | 7/1999 |
| EP | 0 925 729 | 6/1999 |
| WO | WO 01/03524 | 1/2001 |
| EP | 0 933 072 | 8/1999 |
| WO | WO 01/58401 | 8/2001 |
| EP | 1 048 231 | 11/2000 |
| WO | WO 01/61093 | 8/2001 |
| EP | 1 060 677 | 12/2000 |
| WO | WO 01/67900 | 9/2001 |
| EP | 1 060 679 | 12/2000 |
| WO | WO 01/87217 | 11/2001 |
| EP | 1 108 371 | 6/2001 |
| WO | WO 01/87218 | 11/2001 |
| EP | 1 108 372 | 6/2001 |
| WO | WO 01/87562 | 11/2001 |
| EP | 1 108 373 | 6/2001 |
| WO | WO 01/87753 | 11/2001 |
| EP | 1 110 463 | 6/2001 |
| WO | WO 01/88245 | 11/2001 |
| EP | 1 118 277 | 7/2001 |
| WO | WO 02/49565 | 6/2002 |
| EP | 1 125 571 | 8/2001 |
| WO | WO 02/052967 | 7/2002 |
| EP | 1 159 883 | 12/2001 |
| WO | WO 03/041625 A1 | 5/2003 |
| EP | 1 166 730 | 1/2002 |
| WO | WO 03/057107 | 7/2003 |
| EP | 1 179 302 | 2/2002 |
| WO | WO 2004/062398 | 7/2004 |
| EP | 1 184 012 | 3/2002 |
| WO | WO 2004/073430 A2 | 9/2004 |
| EP | 1 188 427 | 3/2002 |
| FR | 1276791 | 10/1960 |
| GB | 238557 | 8/1926 |

OTHER PUBLICATIONS

US 5,915,536, 06/1999, Alberts et al. (withdrawn)

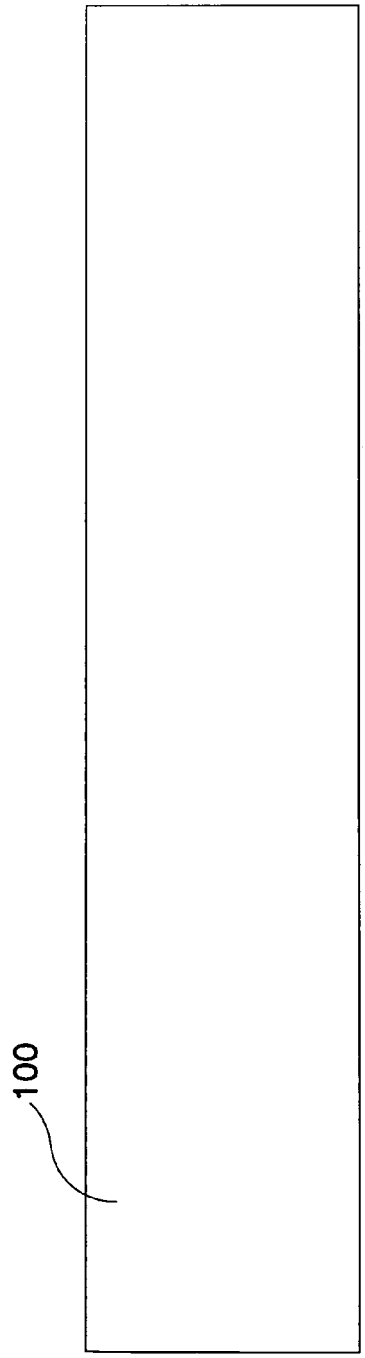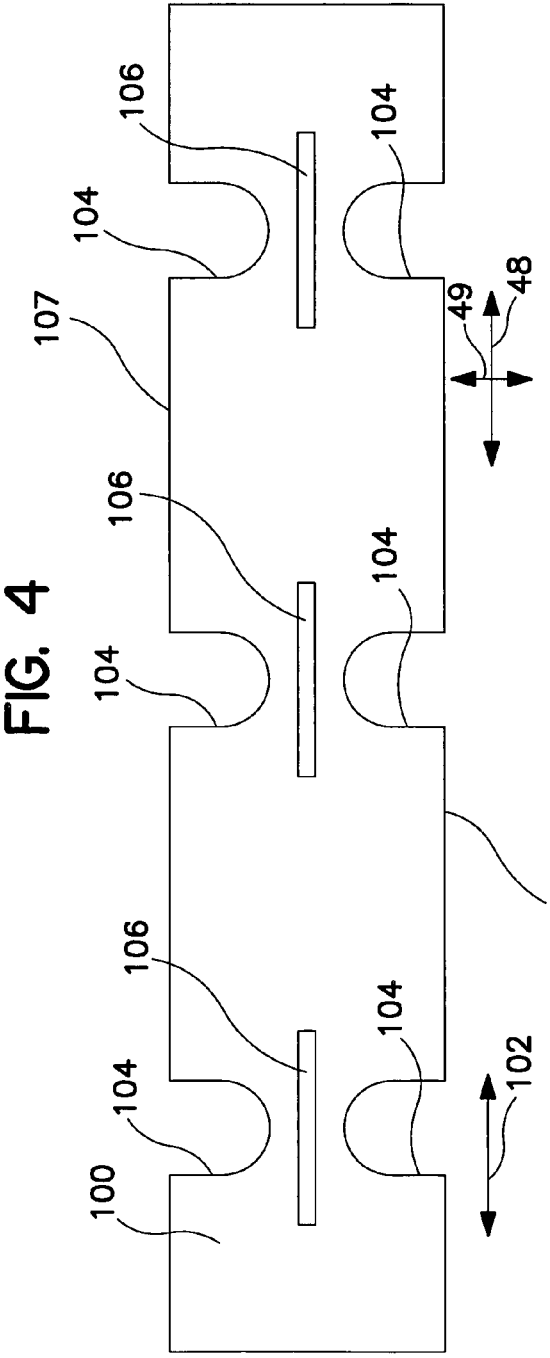

BOXER SHORTS AND PROCESS OF MAKING BOXER SHORTS WITH EXPANDABLE MATERIAL

RELATED APPLICATION

This application is a continuation-in-part of U.S. patent application Ser. No. 10/314,915, filed 9 Dec. 2002 now abandoned. The disclosure of the prior application is incorporated herein by reference.

BACKGROUND OF THE INVENTION

This invention is directed to boxer shorts and methods of making boxer shorts having side seams and selectively expanded areas. The boxer shorts may be absorbent or non-absorbent.

Pant-like garments have numerous applications including disposable clothing, training pants, feminine care products, adult incontinence products, disposable swimwear, or the like. Pant-like disposable garments are typically three-dimensional products with closed sides so that the product has a unitary waist opening and two leg openings. The wearer raises and lowers the garment to apply the product. Three-dimensional, boxer shorts-like products are particularly appealing because the boxer shorts look more like conventional articles of clothing than other types of disposable absorbent articles.

Many disposable pants are formed as composite structures in which several components are combined to form a product specifically suited to its intended purpose. For example, disposable pants often include one or more absorbent materials intended to absorb various bodily exudates such as urine, menstrual fluid, and/or sweat. Such products may include a liquid permeable bodyside liner and a liquid impermeable outer cover, and can include other materials and features such as elastic materials and containment structures.

However, many disposable pants are aesthetically unappealing. Existing disposable absorbent pants can be overly bulky and often resemble disposable baby diapers. Various attempts have been made to provide disposable pants having an improved, more clothing-like appearance. However, disposable pants, particularly disposable absorbent boxer shorts, present many manufacturing challenges. In part, this is due to the high speed that is necessary to economically produce relatively low-cost disposable absorbent products. Product design is often compromised by cost and manufacturing constraints, resulting in disposable pants that lack aesthetic appeal and product function. In addition, crotch depth is required for a good fit, but difficult to achieve in a garment like boxer-shorts with hanging legs when using conventional manufacturing processes.

There is thus a need or desire for garment-like, aesthetically appealing boxer shorts, as well as methods of efficiently manufacturing such boxer shorts.

SUMMARY OF THE INVENTION

In response to the discussed difficulties and problems encountered in the prior art, new pants, and methods for manufacturing such pants, have been invented. The material for the garment shell of the pant is handled as a single web, or a continuous web of multiple pants, throughout assembly until seaming in order to streamline the assembly. The web itself may be an expandable material that can be expanded in selected areas, or an expandable material can be attached to the web, either in a crotch region or in a back region, or both, to provide a conforming fit on a wearer. The pants can include an absorbent assembly and can be made in either the machine direction or the cross direction.

One aspect of the invention pertains to a pant made from a web. One embodiment of the pant includes: a garment shell having a front region, a back region, and a crotch region positioned between the front and back regions, with a front waist edge, a back waist edge, and side seams connecting the front region to the back region. The garment shell also includes two leg openings and hanging legs. At least a portion of each of the front region, the back region, and the hanging legs include portions of the web. The garment shell may be composed of an expandable material in the front region, the back region, and the crotch region, with certain areas of the garment shell selectively expanded, such as in the crotch region and/or the back region, to provide a comfortable fit. Alternatively, an expandable material may be attached to the web, either in the crotch region, the back region, or in both the crotch region and the back region.

For example, the expandable material may be selectively expanded in, or attached to, transversely opposed edges of the web in the crotch region of the garment shell. Alternatively, the expandable material may be selectively expanded across, or attached to form, a full transverse width of the crotch region. The garment may also include a strip attached to the crotch region, approximately midway between the leg openings.

Instead of or in addition to the expandable material in the crotch region, expandable material may be selectively expanded in, or attached to, the back region to provide additional space in the back of the product for improved fit. This placement of expandable material may be particularly advantageous to a wearer's comfort in a sitting position. Additionally, garments including expandable material in the back region may also include a contracted crotch region.

Examples of suitable expandable materials include a stretch-and-set material, which is a material that may be set in its stretched dimension, such as by application of heat. Polyethylene terephthalate (PET) is an example of a material that can be used to produce a stretch-and-set material. Another example of a suitable expandable material is necked material that can expand perpendicular to the direction of necking. Yet another example of a suitable expandable material is material that is selectively corrugated or deformed along at least one edge, such as by enmeshing the material between mating grooved rolls.

The pant may also include an absorbent structure attached to the garment shell.

Another aspect of the invention pertains to a method of making a pant having side seams and hanging legs. One embodiment of the method comprises: providing a web having a crotch region positioned between a front region and a back region; defining two leg openings along transversely opposed edges of the web in the crotch region; providing an expandable material either in the crotch region or in the back region, or in both the crotch region and the back region; and attaching the front region and the back region together to form the side seams. The expandable material, or at least a portion of the expandable material, may be expanded prior to, during, or subsequent to providing the expandable material in the crotch and/or back region.

The invention relates to a wide variety of absorbent and non-absorbent pants, including training pants, swim pants, diaper pants, incontinence garments, feminine care products, health care garments, apparel for institutional, industrial, and consumer use, or other garments. Disposable absorbent pants are adapted to be worn adjacent to the body of a wearer to absorb and contain various exudates discharged from the body.

BRIEF DESCRIPTION OF THE DRAWINGS

These and other objects and features of this invention will be better understood from the following detailed description taken in conjunction with the drawings, wherein:

FIG. 4 is a top view of a web.

FIG. 5 is a top view of the web of FIG. 4 including leg openings and strips applied to the web for assembling pants according to one embodiment of the invention using a machine direction assembly.

DEFINITIONS

Figure 1:
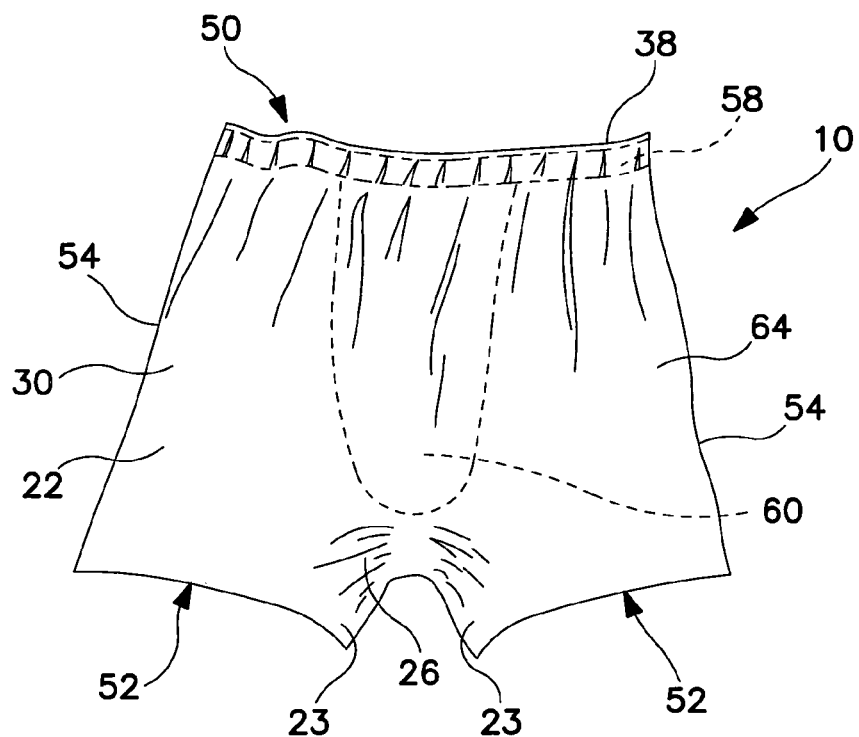
FIG. 1 is a front view of one embodiment of a pant according to the invention.

Within the context of this specification, each term or phrase below will include the following meaning or meanings.

"Attached" refers to the joining, adhering, connecting, bonding, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Boxer shorts" refers to a garment having hanging legs.

"Coform" is a composite material that is essentially an air-formed matrix of thermoplastic polymer microfibers, including meltblown fibers, and a multiplicity of individualized cellulose and/or staple fibers and/or particulates such as superabsorbents disposed throughout the matrix of microfibers and engaging at least some of the microfibers to space the microfibers to intertwine and hold captive within the matrix of microfibers by mechanical entanglement of the microfibers with the cellulose and/or staple fibers and/or particulates including superabsorbent.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Corrugated" refers to the condition of a material which has been gathered into pleats or regular rugosities or folds, the material being shortened thereby.

"Cut-out" refers to a cut portion that includes one portion of a web removed from a remainder of the web, as opposed to a "slit," which is a cut in a web that does not result in the removal of any portion of the web.

"Disposable" refers to articles which are designed to be discarded after a limited use rather than being laundered or otherwise restored for reuse.

"Elastic," "elasticized," and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Expandable" refers to a material that has the ability to expand or stretch. Examples of expandable materials include stretch-and-set materials, corrugated materials, and necked materials.

"Fabric" is used to refer to all woven, knitted and nonwoven fibrous webs.

"Garment shell" refers to an outer cover or outer layer of a garment. In a single-ply garment, the single layer of the garment is the garment shell.

"Garment insert" refers to an inner layer of a garment. The garment insert provides a close-to-the-body fit about a wearer's lower torso, thereby serving as a form of built-in underwear within the garment.

"Hanging legs" refers to the portions of a garment which extend from the crotch region downward to the leg openings. "Downward" refers to a direction toward the ground when the garment is positioned on a standing wearer.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "non-wettable" or hydrophobic.

"Integral" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 3A:
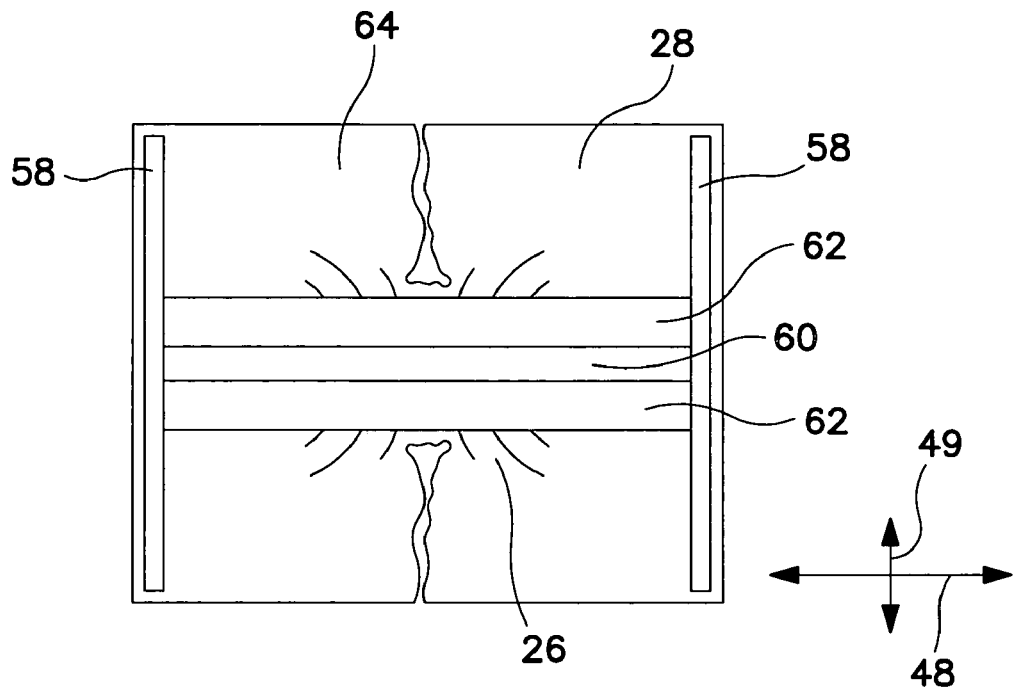
FIG. 3A is a plan view of the garment shown in FIG. 2A, showing the side facing the wearer.
Figure 3B:
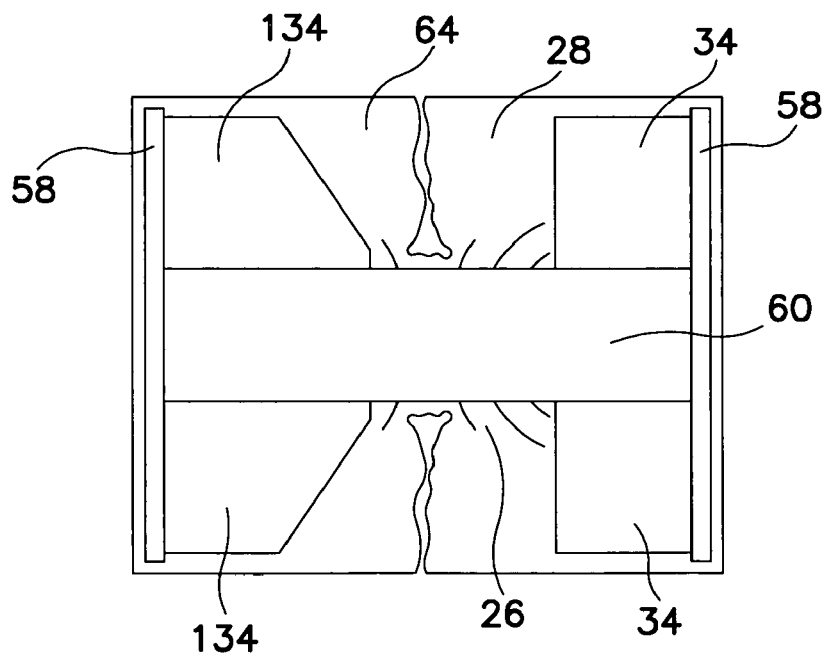
FIG. 3B is a plan view of the garment shown in FIG. 2B, showing the side facing the wearer.
Figure 3C:
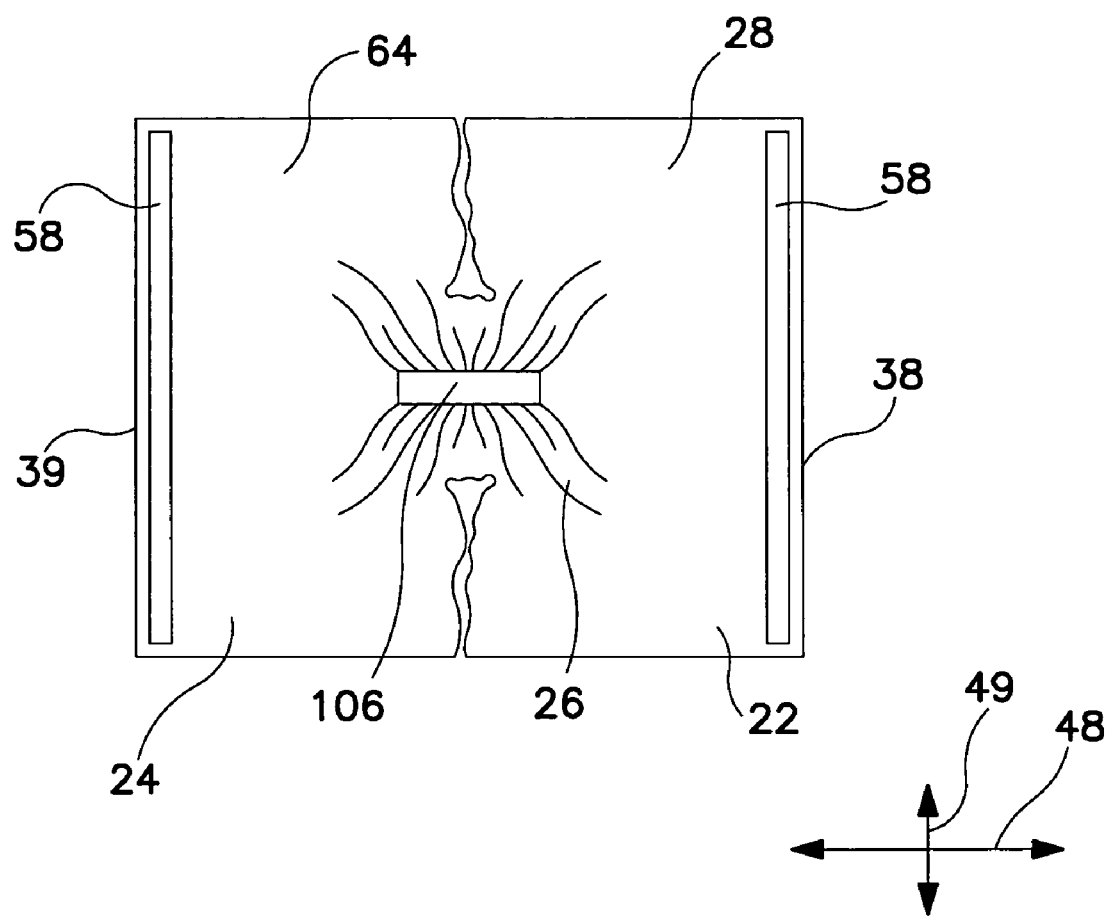
FIG. 3C is a plan view of the garment shown in FIG. 2A, showing the side facing the wearer without an absorbent structure.

"Longitudinal" and "transverse" have their customary meaning, as indicated by the longitudinal and transverse axes depicted in FIGS. 3A and 3C, and are defined with respect to the garment shell. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Machine direction" refers to the length of a fabric in the direction in which it is produced, as opposed to "cross direction" which refers to the width of a fabric in a direction generally perpendicular to the machine direction.

Figure 10:
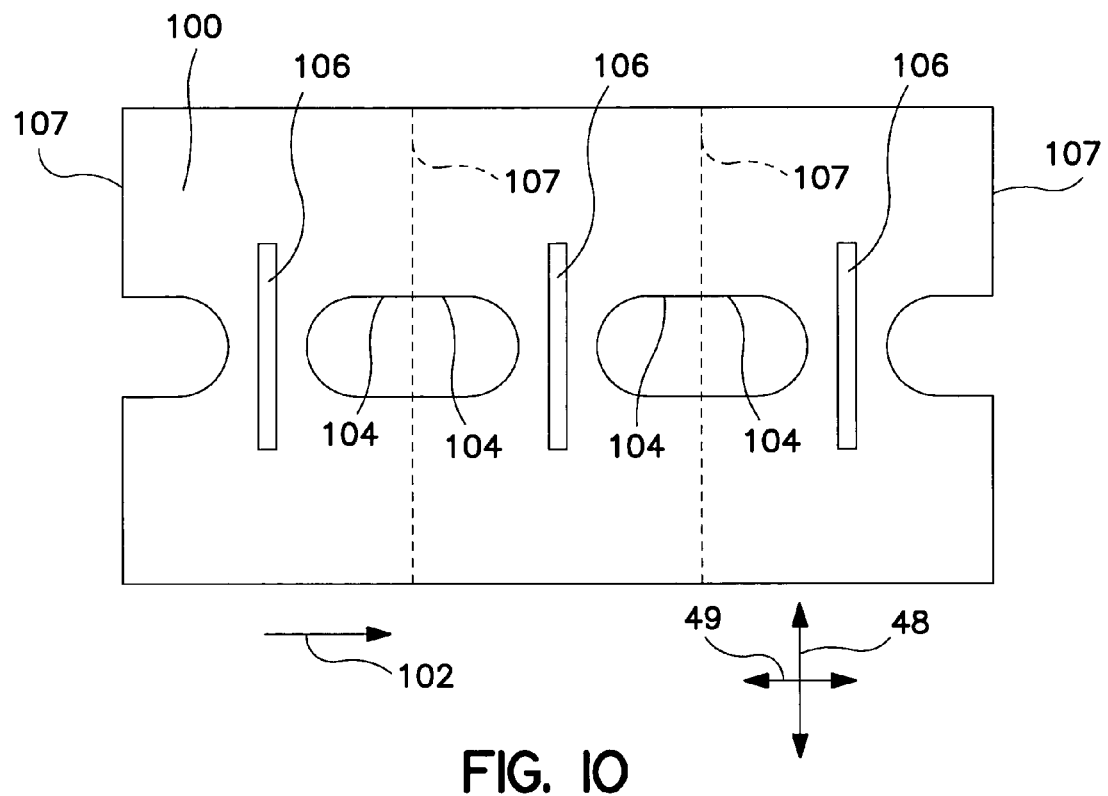
FIG. 10 is a top view of the web of FIG. 4 including leg openings and strips applied to the web for assembling pants according to one embodiment of the invention using a cross direction assembly.

The term "machine direction assembly" refers to a manufacturing process in which disposable products travel in an end-to-end or waist-to-waist orientation, in the longitudinal direction shown by arrow 48 in FIG. 5. A process utilizing a machine direction assembly entails products traveling in a machine direction through a converting machine with their longitudinal axes 48 (FIGS. 3A, 3C) parallel to the direction of arrow 102 (FIG. 5). "Cross direction assembly" entails the products traveling in a machine direction in a side-by-side orientation with their lateral axes 49 (FIGS. 3A, 3C) parallel to the direction of arrow 102, such as is illustrated in FIG. 10.

"Member" when used in the singular can have the dual meaning of a single element or a plurality of elements.

"Necked" refers to a material that has been narrowed in at least one dimension by application of a tensioning force in another direction.

"Nonwoven" and "nonwoven web" and "web" refer to materials and webs of material which are formed without the aid of a textile weaving or knitting process.

"Operatively joined," with reference to the attachment of an elastic member to another element, means that the elastic member can be attached to or connected to the element, and can additionally be treated with heat or chemicals, by pre-stretching, or the like, to give the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as joining either member directly to an element, or can be indirect by means of an additional member disposed between the member and the element.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

"Stabilize" refers to the prevention of further expansion by treating an expandable material in such a manner that the level of expansion remains set in a particular unstretched, semi-stretched, or stretched state.

"Stretch-and-set" refers to a material that may be set in its stretched dimension, such as by application of heat.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Three-dimensional garment" refers to a garment that cannot be laid flat with all of its seams in one plane.

These terms may be defined with additional language in the remaining portions of the specification.

DESCRIPTION OF PREFERRED EMBODIMENTS

Figure 2A:
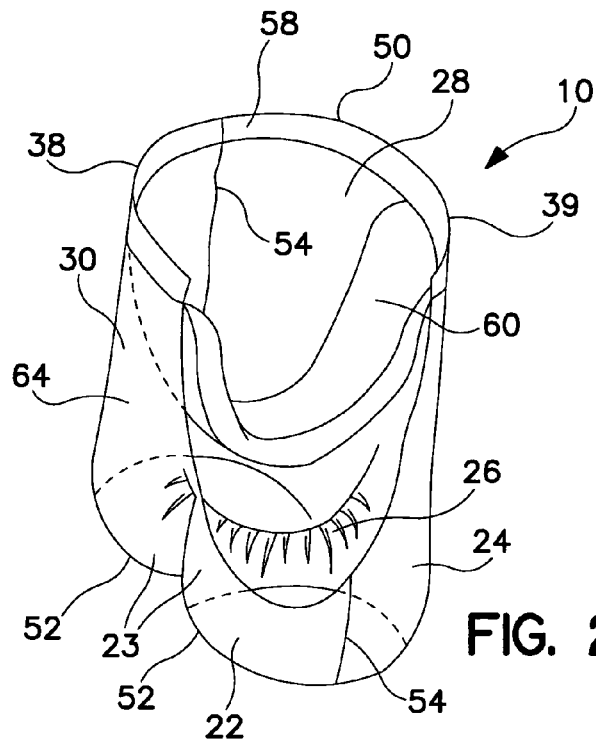
FIG. 2A is a perspective cut-away view of one embodiment of a pant according to the invention.
Figure 2B:
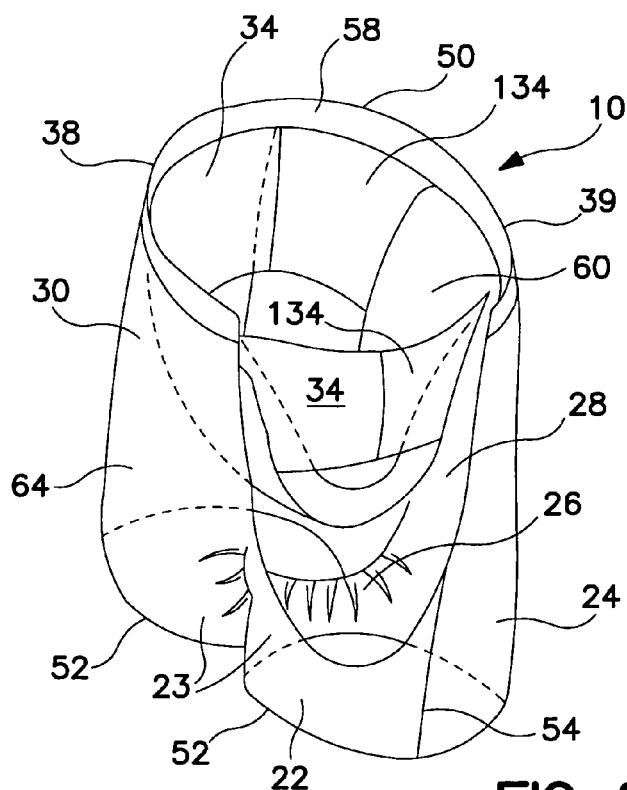
FIG. 2B is a perspective cut-away view of one embodiment of a pant according to the invention.

As representatively illustrated in FIGS. 1, 2A, and 2B, an embodiment of a pant 10 of the invention includes a garment shell 64. The garment shell 64 can include a front region 22, a back region 24, a crotch region 26, an inner surface 28 which is configured to contact the wearer, and an outer surface 30 opposite the inner surface 28 which is configured to contact the wearer's clothing. The pant 10 also defines a pair of longitudinally opposed waist edges, which are designated front waist edge 38 and back waist edge 39. The front region 22 is contiguous with the front waist edge 38, and the back region 24 is contiguous with the back waist edge 39. The front region 22 includes the portion of the pant 10 which, when worn, is positioned on the front of the wearer while the back region 24 includes the portion of the pant 10 which, when worn, is positioned on the back of the wearer. The crotch region 26 of the pant 10 includes the portion of the pant which, when worn, is positioned between the legs of the wearer and covers the lower torso of the wearer. As illustrated in FIGS. 1, 2A, and 2B the front and back regions 22 and 24 are joined together at side seams 54 to define a three-dimensional pant configuration having a waist opening 50 and a pair of leg openings 52. In particular embodiments, the pant 10 can include an absorbent structure 60.

As illustrated in FIGS. 13A-F and described more fully below, the garment shell 64 may be composed of an expandable material 68 in the front region 22, the back region 24, and the crotch region 26, with certain areas of the garment shell selectively expanded, such as in the crotch region 26 and/or the back region 24, to provide a comfortable fit. Alternatively, an expandable material 68 may be attached to a web 100, either in the crotch region 26, the back region 24, or in both the crotch region 26 and the back region 24.

In certain embodiments, also described more fully below, the crotch region 26 may be contracted, either elastically or inelastically. The expandable material 68 and/or the contraction of crotch region 26 provide a crotch depth that provides a good fit through the crotch region 26, thereby allowing the front and back regions to hang properly. The garment shell 64 can also include hanging legs 23 which extend from the crotch region 26 downward to the leg openings 52 (FIGS. 1, 2A, and 2B).

The pant 10 also includes side seams 54 that connect the front region 22 to the back region 24 to create the pant 10. The side seams 54 can take any number of forms, including both refastenable and non-refastenable seams, as are known in the art. The provision of the side seams 54 can be accomplished in the manner described in U.S. Pat. No. 6,192,521 issued 27 Feb. 2001 to Alberts et al.; U.S. Pat. No. 5,046,272, issued 10 Sep. 1991 to Vogt et al., which is incorporated herein by reference, or in the manner described in U.S. Pat. No. 6,565,691, issued 20 May 2003 to Tomsovic, et al.; U.S. Pat. No. 6,723,034 issued 20 Apr. 2004 to Durrance, et al.; U.S. Pat. No. 6,596,113 issued 22 Jul. 2003 to Csida, et al.; and/or U.S. Pat. No. 6,513,221 issued 4 Feb. 2003 to Vogt, et al.; all of which are incorporated herein by reference. As is known in the art, the side seams 54 can be inward or outward fin seams or lap seams (not shown).

The pant 10 can also have a waist elastic member 58 extending along at least a portion of the front waist edge 38 and/or the back waist edge 39. The waist elastic member 58 can be formed of any suitable elastic material. As is well known to those skilled in the art, suitable elastic materials include sheets, strands, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the waist elastic member 58 includes a plurality of dry-spun coalesced multifilament spandex elastomeric threads sold under the trade name LYCRA® and available from Invista Corporation, Wilmington, Del., U.S.A. Alternatively, multiple strands of 310 decitex LYCRA® may be also laminated at 250% elongation between spunbond facings in addition to an adhesive.

As another alternative, the waist elastic member 58 can be a material exhibiting delayed retraction, or can in fact be non-elastic. Delayed retraction materials may include those designed to retract relatively slowly following compression, such as "temporarily inhibited" elastic materials. "Temporarily inhibited" materials are described, for example, in U.S. Pat. No. 5,545,158 issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, all of which are herein incorporated by reference, and references cited therein. Alternatively, a delayed retraction material may be designed to resist retraction until an activation process occurs, such as so-called "latent elastic" materials. Suitable retractive materials for use as a delayed retraction material can alternatively comprise any material adapted to retract upon activation, whether immediately upon activation or subsequently thereto. The retractive material may include elastomeric or nonelastomeric materials. Suitable nonelastomeric retractive materials may include without limitation polyether block amides (PEBAX®) or the like, and laminates thereof. Suitable elastomeric retractive materials may include without limitation LYCRA® materials, elastomeric materials including latex or rubber or synthetic urethanes, or the like, and laminates thereof. In particular embodiments, the retractive material may include an elastomeric material having an unstable state relative to some other stable and elastic state. In such embodiments, the retractive material can, but need not, have elastomeric properties in the unstable state. Other examples include heat-shrinkable elastic materials such as described in U.S. Pat. No. 4,816,094 issued Mar. 28, 1989 to Pomplun et al., U.S. Pat. No. 4,665,306 issued May 12, 1987 to Roland et al., and U.S. Pat. No. 4,663,106 issued May 5, 1987 to Pomplun et al., all of which are herein incorporated by reference.

A pant of this type can be designed to fit wearers in a wide range of sizes by adjusting the pant dimensions based on the anthropometric features of an intended wearer. Ratios of wearer dimensions to pant dimensions for a suitable boxer-style pant have been determined and are shown in Table 1. In addition, stylistic variations such as hip-hugging (low rise), relatively more closely or loosely fitted shorts, and other styles, may be provided by varying the ratios listed in Table 1 within (or even beyond) the ranges shown. Moreover, the use of elastomeric or extensible material to form the garment shell may provide additional adaptability to fit a wider range of wearer sizes.

Figure 1A:
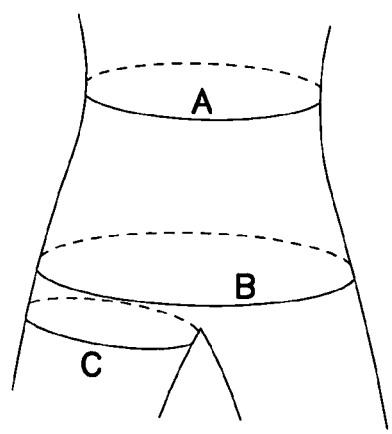
FIGS. 1A and 1B illustrate dimensions described with respect to Tables 1 and 2.
Figure 1B:
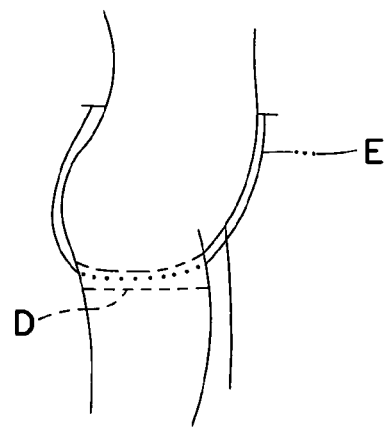
Figures 5A, 5B:
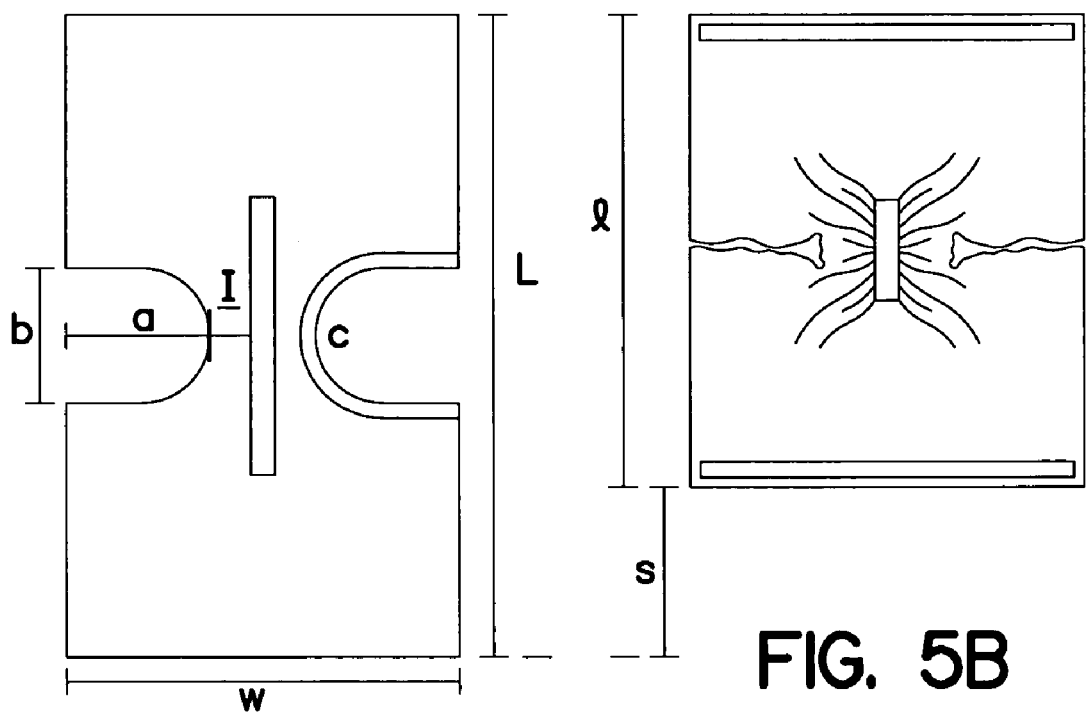
FIGS. 5A and 5B illustrate dimensions described with respect to Tables 1 and 2.

Since the pant dimensions are determined by the dimensions of the intended wearer, the ratios shown are based upon five measurements of an intended wearer, abbreviated as follows:

A: waist circumference (FIG. 1A)
B: hip circumference (FIG. 1A)
C: thigh circumference (measured in crotch region, horizontally; see FIG. 1A)
D: crotch depth (measured in crotch region, viewed 18 inches from the wearer's side; see FIG. 1B)
E: center front waist to center back waist through crotch; see FIG. 1B Table 2 shows how garment shell dimensions shown in FIGS. 5A and 5B are determined using body measurements A-E and ratios in Table 1. Table 2 also shows how the ratios in Table 1 have been applied to create shorts for two different size wearers, one a mannequin of a child (Wearer #1) weighing approximately 32 to 40 pounds (15-18 Kg), the other an adult female (Wearer #2) weighing approximately 125 pounds (57 Kg).

TABLE 1

| PANT DIMENSIONS | DETAILS and RATIOS | EXEMPLARY RANGES |
|---|---|---|
| Garment inseam I (FIG. 5A, dimension "I") | Selected based on garment style. There is not a seam at this location; this is simply the location where an "inseam" measurement is generally taken. After contraction, this dimension "I" provides the "hanging legs" feature of the pant. | 1–5 inches, or more |
| Width of garment shell | Ratio of 2 × Width (i.e., | From about 1.2:1 to about |

TABLE 1-continued

| PANT DIMENSIONS | DETAILS and RATIOS | EXEMPLARY RANGES |
|---|---|---|
| (FIG. 5A, dimension "w") | garment circumference) to the larger of wearer's Hip or Waist circumference 2w:[B or A] | 2:1, such as about 1.7, e.g. 2w = 1.2A or 1.2B |
| Length of base of arc (FIG. 5A, dimension "b") | Ratio of Arc base length to Wearer crotch depth b:D | From about 1:1 to about 1.5:1, such as about 1.25:1 |
| Circumference of leg opening (FIG. 5A, dimension "c") | Ratio of Leg opening to Wearer thigh circumference c:C | From about 1.1:1 to about 1.5:1, such as about 1.25:1 |
| Takeup (shortening) of garment shell on gathering of crotch (FIG. 5B, dimension "s") | Ratio of Takeup to 2 × Garment inseam length I s:2I | From about 1:1 to about 1.6:1, such as about 1.3:1 |
| Length of garment shell after gathering (FIG. 5B, dimension "l") | Ratio of Length after gathering to Wearer F to B waist thru crotch l:E | This can vary widely depending on the desired short style, but for a standard fit, from about 1.1:1 to about 1.4:1, such as about 1.25:1, e.g. l = 1.4E |
| Length of garment shell before gathering (FIG. 5A, dimension "L") | Sum of Takeup and Length of shell after gathering s + l | |
| Arc height (FIG. 5A, dimension "a") | (Width of garment shell – 2 × Garment inseam I)/2 (w – 2I)/2 | |

TABLE 2

| | Wearer #1 | Short #1 | Wearer #2 | Short #2 |
|---|---|---|---|---|
| A | 50 cm | | 78 cm | |
| B | 54 cm | | 96 cm | |
| C | 29 cm | | 55 cm | |
| D | 10 cm | | 16.5 cm | |
| E | 41 cm | | 61 cm | |
| I | | 6 cm | | 8 cm |
| w | | 45 cm | | 67 cm |
| b | | 12.5 cm | | 20.5 cm |
| c | | 36 cm | | 68 cm |
| s | | 15.5 cm | | 21 cm |
| l | | 50.5 cm | | 75 cm |
| L | | 66 cm | | 96 cm |
| a | | 15 cm | | 25 cm |

The pant 10 can also include an absorbent structure 60. The absorbent structure 60 can be attached to the garment shell 64 at the front waist edge 38 and back waist edge 39, or at some point below the front waist edge 38 and back waist edge 39 on the front region 22 and back region 24. (FIGS. 2A and 2B). Alternatively, the absorbent structure 60 can be attached to the garment shell 64 in the crotch region 26. The absorbent structure 60 may be either permanently attached to the garment shell 64 or refastenably attached to the garment shell 64 to allow for replacement of the absorbent structure 60 when the absorbent structure 60 becomes soiled.

The absorbent structure 60 can be any structure that is generally compressible, conformable, non-irritating to the skin, and capable of absorbing and retaining liquids and certain body wastes. The absorbent structure 60 can be manufactured in a wide variety of sizes and shapes, from a wide variety of liquid absorbent materials commonly used in the art, and may be stretchable, non-stretchable, or elastic. For example, the absorbent structure 60 can suitably include a matrix of hydrophilic fibers, such as a web of cellulosic fluff, mixed with particles of a high-absorbency material commonly known as superabsorbent material. In a particular embodiment, the absorbent structure 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 60 to better contain and absorb body exudates. The concentration of the superabsorbent particles can also vary through the thickness of the absorbent structure 60. Alternatively, the absorbent structure 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen, Inc. in Greensboro, N.C., U.S.A. Typically, a superabsorbent material is capable of absorbing at least about 15 times its weight in water, and desirably is capable of absorbing more than about 25 times its weight in water.

In one embodiment, the absorbent structure 60 includes a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent structure 60 in an amount of from 0 to about 90 weight percent based on total weight of the absorbent assembly. The absorbent structure 60 suitably has a density within the range of about 0.10 to about 0.35 grams per cubic centimeter. The absorbent structure 60 may or may not be wrapped or encompassed by a suitable tissue or nonwoven wrap that may help maintain the integrity and/or shape of the absorbent assembly.

The absorbent structure 60 can also incorporate other materials that are designed primarily to receive, temporarily store, and/or transport liquid along the mutually facing surface with absorbent structure 60, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

In particular embodiments, the absorbent structure 60 is thin to provide a slim, comfortable, non-bulky pant 10. Any suitable thin absorbent structure may be used, such as for example, the thin absorbent described in WO 02/49565, published Jun. 27, 2002, by Sawyer et al., which is incorporated herein by reference.

The absorbent structure 60 can include a pair of containment flaps 62 (FIG. 3A) which are configured to provide a barrier to the transverse flow of body exudates. A flap elastic member (not shown) can be operatively joined with each containment flap 62 in any suitable manner as is well known in the art. The elasticized containment flaps 62 define an unattached edge which assumes an upright, generally perpendicular configuration to form a seal against the wearer's body. Suitable constructions and arrangements for the containment flaps 62 are generally well known to those skilled in the art and are described in U.S. Pat. No. 4,704,116 issued Nov. 3, 1987, to Enloe, which is incorporated herein by reference.

As an alternative, a pant-like garment insert could be used for the absorbent structure 60. For example, the pant-like garment insert may include a body side liner, an outer cover, and an absorbent assembly between the body side liner and the outer cover, and side panels. Examples of suitable pant-like garment inserts include a training pant, such as HUGGIES® PULL-UPS® Disposable Training Pants, or a disposable underpant, such as GOODNITES® Disposable Underpants, both manufactured by Kimberly-Clark Corporation, Neenah, Wis., U.S.A. A training pant serving as the pant-like garment insert for the absorbent structure 60 can include front side panels 34 and back side panels 134 (FIGS. 2B and 3B). The manufacture of training pants having side panels can be accomplished in the manner described in U.S. Pat. No. 6,562,167, issued 13 May 2003 to Coenen et al., which is incorporated herein by reference.

As another alternative, a pad-type absorbent could be used for the absorbent structure. The pad-type absorbent can be attached in the crotch region 26 of the pant 10. An example of a suitable pad-type absorbent is a feminine care pad such as KOTEX® Feminine Napkins, KOTEX® LIGHTDAYS® disposable panty liners, or an incontinence absorbent pad such as POISE® Feminine Guards and Pads or DEPEND® Guards for Men, all manufactured by Kimberly-Clark Corporation, Neenah, Wis., U.S.A.

For reference, arrows 48 and 49 depicting the orientation of the longitudinal axis and the transverse axis, respectively, of the garment shell 64 are illustrated in FIGS. 3A, 3C, and 5.

The garment shell 64 is suitably constructed of materials that are comfortable against the skin and non-irritating. It is contemplated that the garment shell 64 can be either disposable or durable. Both nonwoven and woven materials are contemplated for the garment shell 64. For example, the garment shell 64 for pant 10 can be selected from a wide variety of materials, including elastic, stretchable, or nonstretchable materials. The garment shell 64 can be a single layer of material or a multi-layered laminate structure. One example of a suitable material is a spunbond polypropylene nonwoven web. The garment shell 64 itself may be absorbent and, for example, may be made of those materials of which the absorbent structure 60 is made. For instance, the garment shell 64 may include a coform material with a polyethylene film on an outer surface of the garment. The garment shell 64 suitably provides a relatively cloth-like texture to the wearer.

Figure 13A:
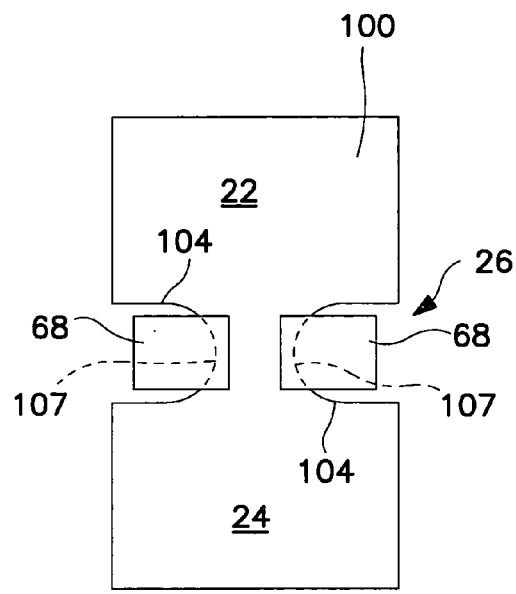
FIGS. 13A-13F are plan views of various embodiments of the garment including expandable material, showing the side of the garment facing the wearer.
Figure 13B:
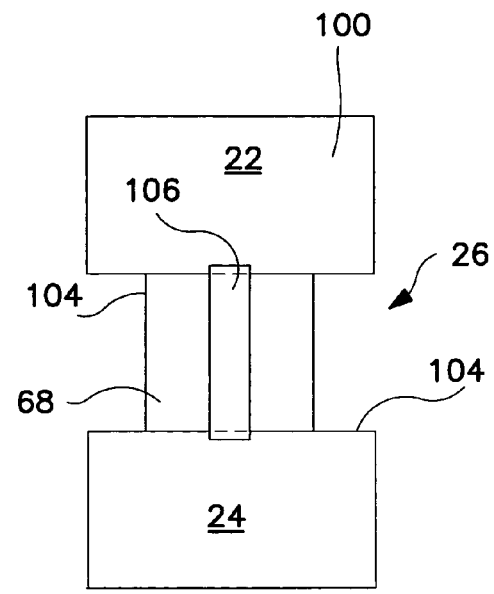

The garment shell 64 may be a single integral piece of expandable material 68. Alternatively, an expandable material 68 may be attached to the garment shell 64 in the crotch region 26 to provide a contoured fit around the leg openings 104 in the crotch region 26 and to expedite high-speed manufacture of the garments. FIG. 13A illustrates the garment shell 64 with expandable material 68 attached to transversely opposed edges 107 of the garment shell 64 in the crotch region 26. Alternatively, the crotch region 26 may be formed of the expandable material 68, as illustrated in FIG. 13B. In the embodiment in FIG. 13B, the expandable material 68 is attached to the front region 22 and the back region 24 of the garment shell 64. A strip 106 may be attached to the crotch region 26 approximately midway between the side seams (in the finished product) to stabilize the central portion of the expandable material 68. Other techniques instead of or in addition to strips 106 may be used to stabilize portions of the expandable material 68, such as bonding corrugated or contracted regions to prevent full expansion of the stabilized regions.

Figure 13C:
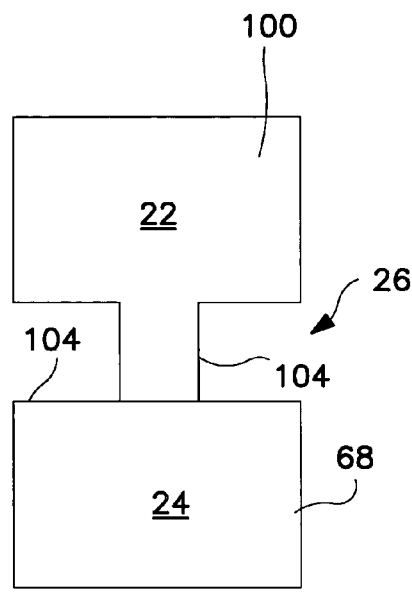
Figure 13D:
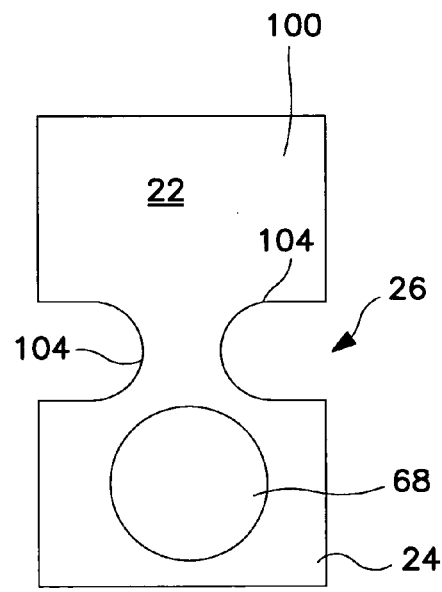

In certain embodiments, expandable material 68 may be included in the back region 24 of the garment shell 64 to provide additional space in the back of the garment. The expandable material 68 may form all of the back region 24, as illustrated in FIG. 13C, or just a portion of the back region 24, as illustrated in FIG. 13D. By including the expandable material 68 in the back region 24, additional room for expansion is provided for the wearer's buttocks, which is particularly advantageous when the wearer is in a sitting position.

The expandable material 68 may be included in the crotch region 26 and/or in the back region 24 of the garment shell 64.

Figure 13E:
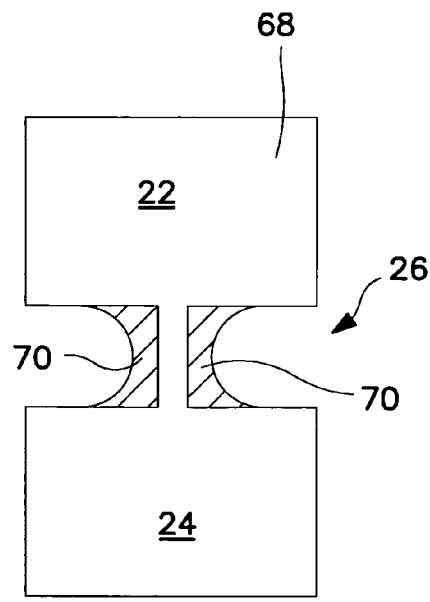
Figure 13F:
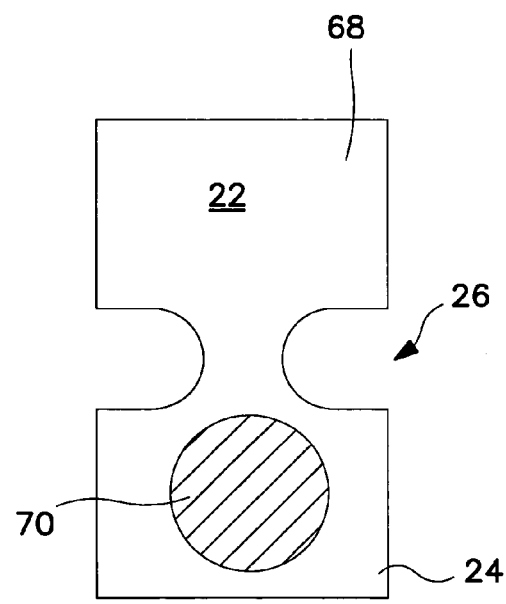

When the garment shell 64 is formed of a single integral piece of expandable material 68, selected areas of the garment shell 64 may be expanded while the remaining areas remain unexpanded. For example, the crotch region 26 may include a selectively expanded area 70, as illustrated in FIG. 13E. As another example, the back region 24 may include a selectively expanded area 70, as illustrated in FIG. 13F. One or more areas of the expandable material 68 may be selectively expanded, such as both the crotch region 26 and the back region 24.

The expandable material 68, whether used to form all or a portion of the garment shell 64, may be any suitable material that can be expanded or permanently stretched. More particularly, the expandable material 68 may be expanded and set, or may be expanded through plastic deformation or breaking of fibers to cause the desired contouring.

One example of a suitable expandable material 68 is a stretch-and-set material in which the material may be set in its stretched dimension, such as by application of heat. Polyethylene terephthalate (PET) is particularly suitable for forming a stretch-and-set material.

Another example of a suitable expandable material 68 is a necked material that can expand perpendicular to the direction of necking. With necked materials, in particular, it may be helpful to stabilize the necked material along the longitudinal centerline of the garment, such as by attaching a strip 106 to the crotch region 26, so that only the edges of the expandable material 68 adjacent to the leg openings 104 may expand.

Yet another example of a suitable expandable material 68 is a corrugated material that is selectively corrugated or deformed along the edges adjacent to the leg openings 104, such as by enmeshing the material between mating grooved rolls. Examples of suitable corrugation devices and methods are described in U.S. Pat. Nos. 4,116,892; 4,223,059; and 4,285,100 issued to Schwarz, each of which is incorporated herein by reference. These corrugation concepts can be enhanced by using mating rolls that stretch the materials only in the areas desired.

When the garment shell 64 includes separate expandable material 68 attached to other materials, the expandable material 68 may be expanded either prior to, during, or subsequent to attaching the expandable material 68 to other garment shell 64 materials.

The present invention also includes various methods for making pants from a web. Referring to FIG. 4, a single web 100 is provided moving in the direction represented by arrow 102. Alternatively, two webs that are joined at their edges to form a double-width piece (not shown) can be used for the web 100. The web 100 may be composed of any material previously described for the garment shell 64.

The method can be carried out using machine direction assembly so that arrow 102 can correspond to the longitudinal direction parallel to the longitudinal axis 48 as shown in FIG. 5 with the products connected end-to-end or waist-to-waist, or the method can be carried out using cross direction assembly so that arrow 102 can correspond to the transverse direction parallel to the transverse axis 49 as shown in FIG. 10 with the products connected side-to-side.

In both the machine direction process (FIGS. 5, 6-9) and the cross direction process (FIGS. 10-12), the web 100 is cut along each of the transversely opposed edges 107 of the web 100 to define leg openings 104 (FIGS. 5 and 10). More particularly, the leg opening 104 may be formed by slitting or die-cutting or otherwise removing a portion of the web 100 from the remainder of the web 100. The geometry of the leg opening 104 affects the overall product appearance. As more fully described below, the leg openings 104 become the leg openings 52 of the pant 10.

In the machine direction process (FIGS. 5 and 6-9), strips 106 may be applied to selected areas located between the leg openings 104. The strips 106 may be used to stabilize the crotch region 26, thereby reducing stretchability in the crotch region along the strip 106, or to additionally or alternatively contract the crotch region 106. Thus, strips 106 can include elastic or non-elastic material. Examples of suitable non-elastic material include heat contractible materials, such as heat shrinkable films, for example, films formed of polyether block amides (PEBAX®, available from the Atofina Company of France) or the like. If the strips 106 are elastic, the elastic can be formed of any suitable material previously described for the waist elastic member 58. As an alternative, strips 106 can include any of the previously described delayed retraction materials.

Figure 7:
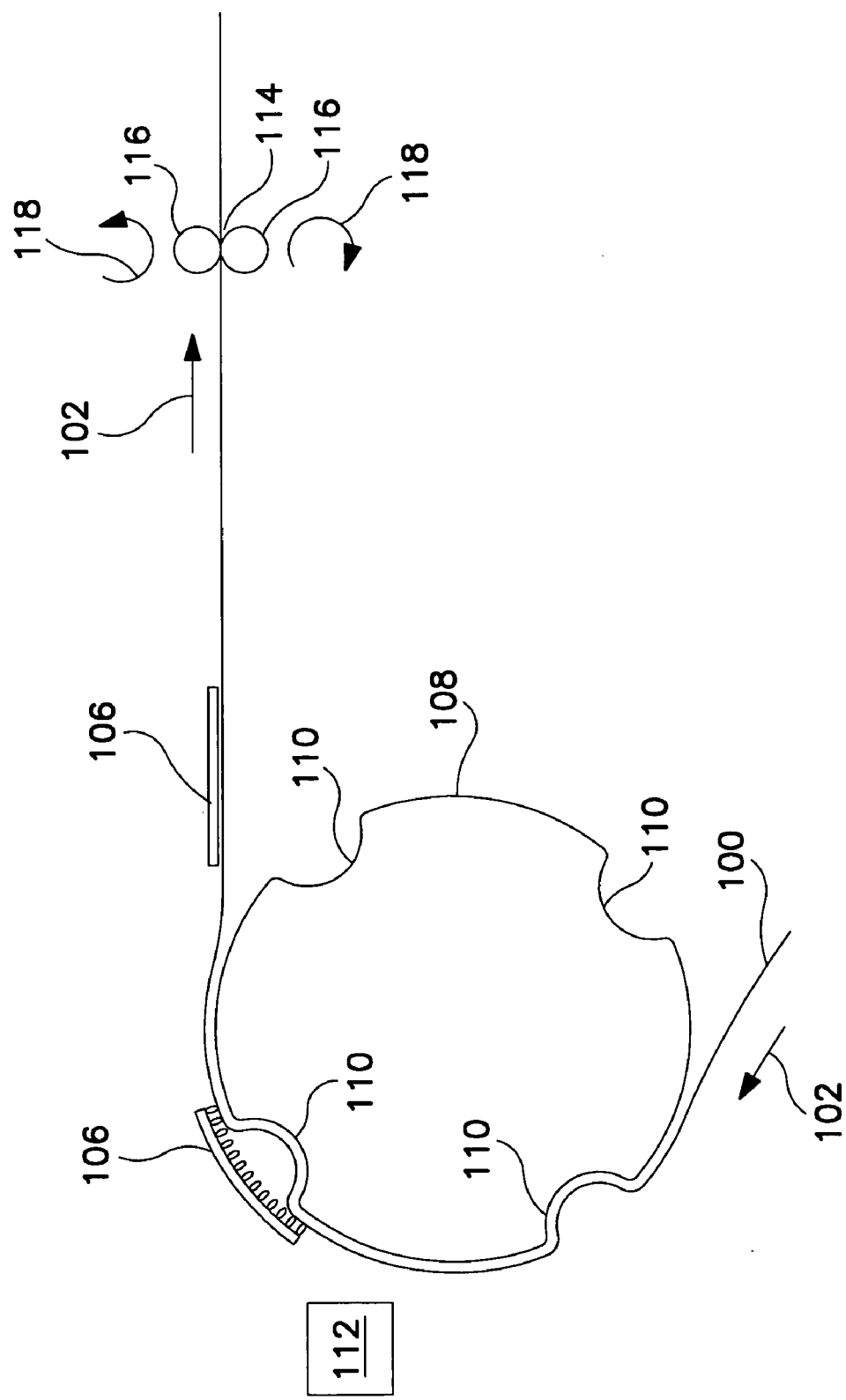
FIG. 7 is a side view of a looper drum for applying an elastic strip to the web.

Referring to FIG. 7, if the strips 106 are elastic, the strips 106 can be applied to the web 100 using a looper drum 108. Looper drums like looper drum 108 are known and are described, for example, in U.S. Pat. No. 5,171,388 issued Dec. 15, 1992 to Hoffman et al., herein incorporated by reference. Drum 108 includes surface grooves 110. Drum 108, as illustrated in FIG. 7, includes four surface grooves 110, but any number of surface grooves 110 may be included. The surface grooves 110 are spaced around the drum 108 so that each garment shell 64 eventually includes one strip 106. The web 100 travels around the drum 108 in the direction of arrow 102. The web 100 runs down into the surface grooves 110 by virtue of the fact that the drum 108 includes apertures across its surface and is under vacuum. Adhesive (shown for purposes of illustration as dots between strip 106 and the web 100 over the surface groove 110) can be applied to the strip 106. Alternatively, the adhesive can be applied to the web 100 in the selected areas between leg openings 104. Suitable adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A.

The web 100 passes by the elastic application module 112 and the strip 106 of elastic is applied in a substantially unstretched condition to the web 100 over the surface groove 110. The web 100 with the strip 106 of elastic continues moving in the direction of arrow 102 out of surface groove 110 and off the drum 108. The web 100 with strip 106 of elastic passes through nip 114 to press and secure the strip 106 of elastic to the web 100. The nip 114 is defined by rolls 116 turning in the direction of arrows 118. In the alternative, any other suitable method for pressing and securing the strip 106 of elastic to the web 100 can be used. As web 100 exits the nip 114, the web 100 can be drawn at a slower rate by the downstream process than the surface speed of rolls 116, allowing the strip 106 of elastic to contract and reduce the length of web 100.

Figure 6:
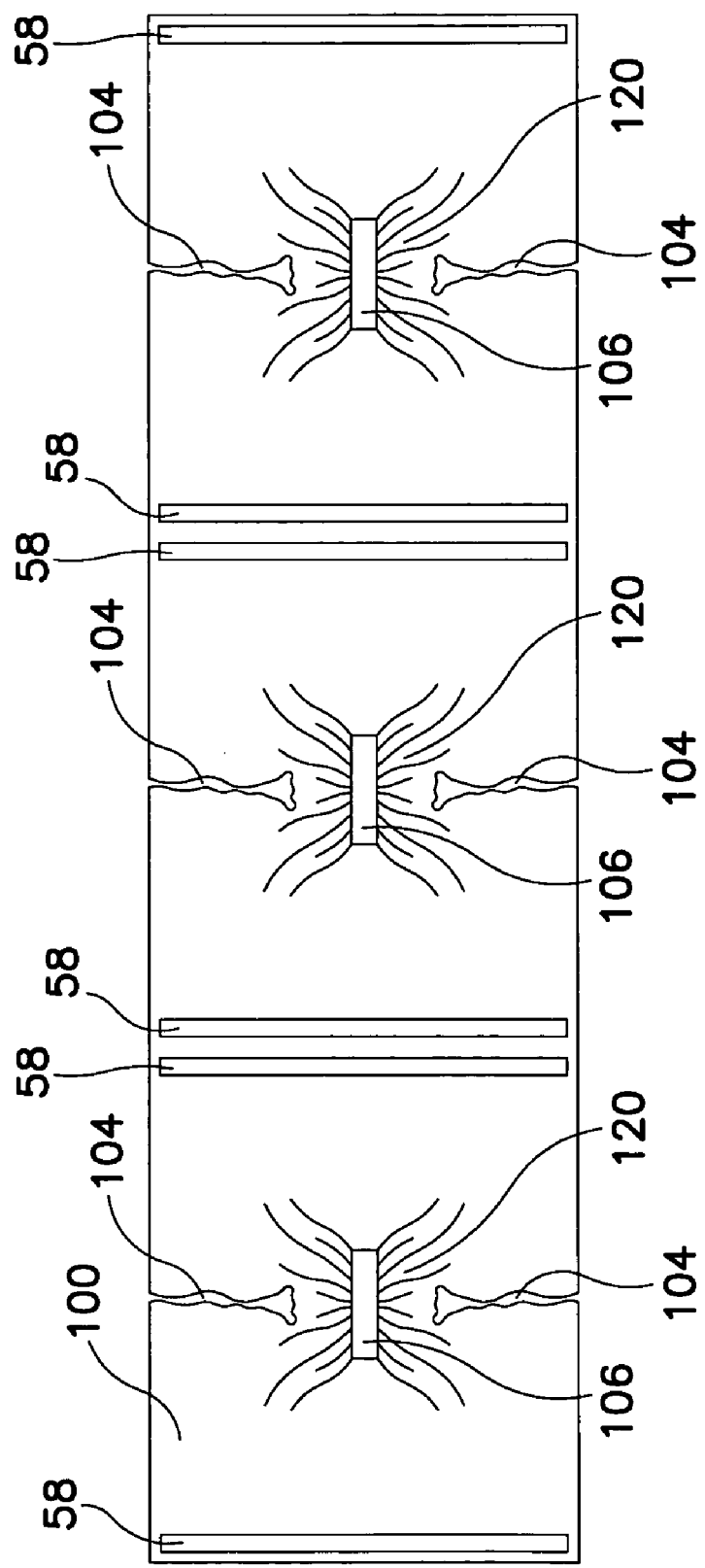
FIG. 6 is a top view of the web of FIG. 5 after contraction of the web.

FIG. 6 shows the web 100 after the contraction of the strips 106. The contraction of the web 100 defines contracted areas 120 in the selected areas between leg openings 104. The contracted area 120, as described more fully below, becomes the crotch region 26 of the pant 10.

Alternatively, the strip 106 can be applied to the web 100 by any other method known in the art such as, for example, a corrugating drum such as that described in U.S. Pat. No. 4,397,704 issued 9 Aug. 1983 to Frick, or an elastic application system in which the material is gathered into folds running in the cross direction and a continuous elastic is applied in the machine direction and severed at the location of the folds in the base material such as described in U.S. Pat. No. 4,417,938 issued 29 Nov. 1983 to Sigl, or an intermittent adhesive application that allows the elastic to snap back from non-adhesive zones, a high efficiency interface roll such as that described in U.S. Pat. No. 6,022,443 issued 8 Feb. 2000 to Rajala et al., U.S. Pat. No. 5,556,504 issued 17 Sep. 1996 to Rajala et al., and U.S. Pat. No. 6,319,347 issued 20 Nov. 2001 to Rajala et al., all of which are here incorporated by reference, or by any other any means known in the art.

Figure 11:
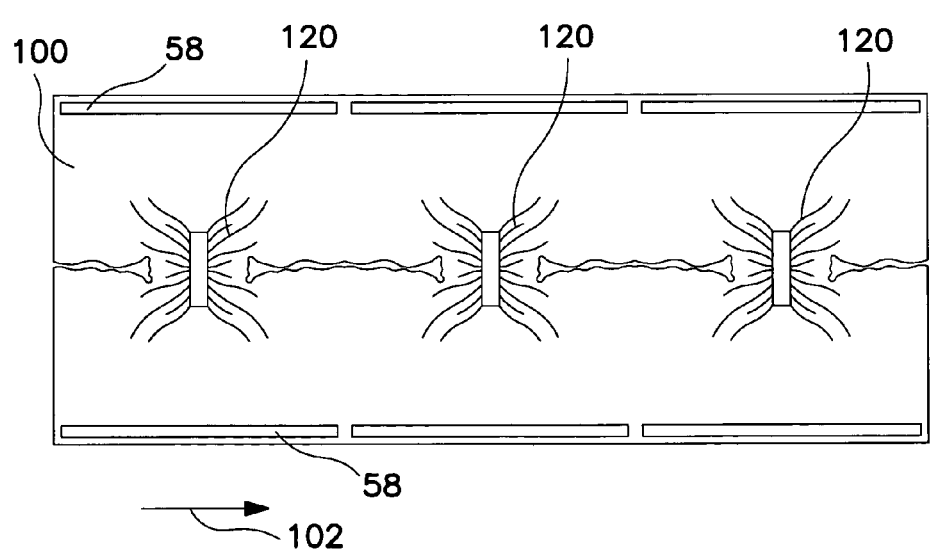
FIG. 11 is a top view of the web of FIG. 10 after contraction of the web.
Figure 12:
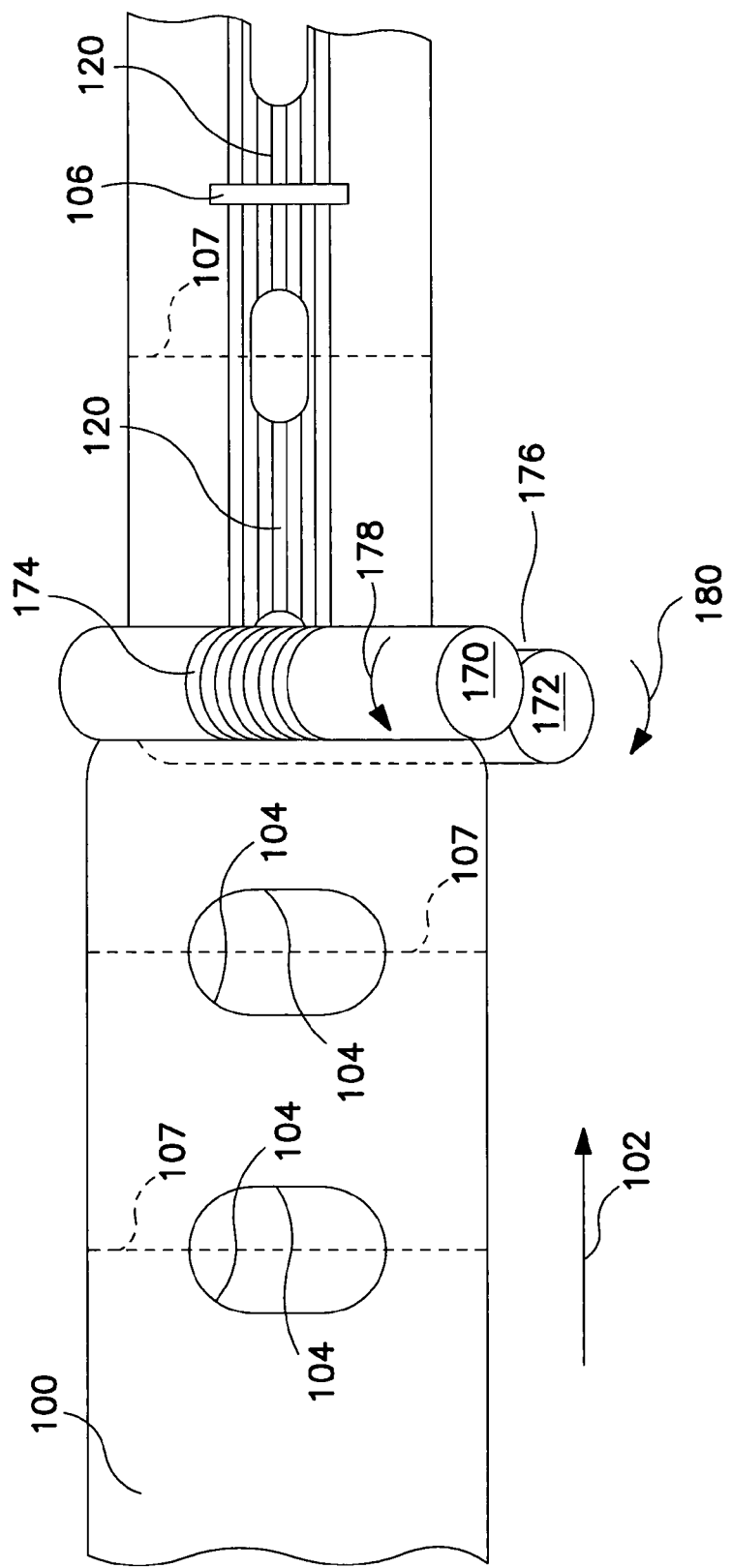
FIG. 12 is a side view of the web of FIG. 10 passing through corrugating rollers for corrugating the web of FIG. 10.

FIGS. 6 and 11 also show waist elastics 58 applied to the web 100. The waist elastics 58 can be applied by any method known in the art at any stage in the manufacturing of the pant 10.

As an alternative, the tension on the web 100 can be reduced by cutting the web 100 into separate pieces approximately midway between successive strips 106 to define a garment shell 64 (FIG. 3C). It is also contemplated, however, that the step of cutting the web 100 can be carried out after contraction of the web 100. It is further contemplated that, instead of a continuous web of multiple garment assemblies connected to one another, the web 100 may exist as a single garment assembly or garment shell 64 at the outset of the process. This option exists in both the machine direction process as well as the cross direction process.

Figure 8:
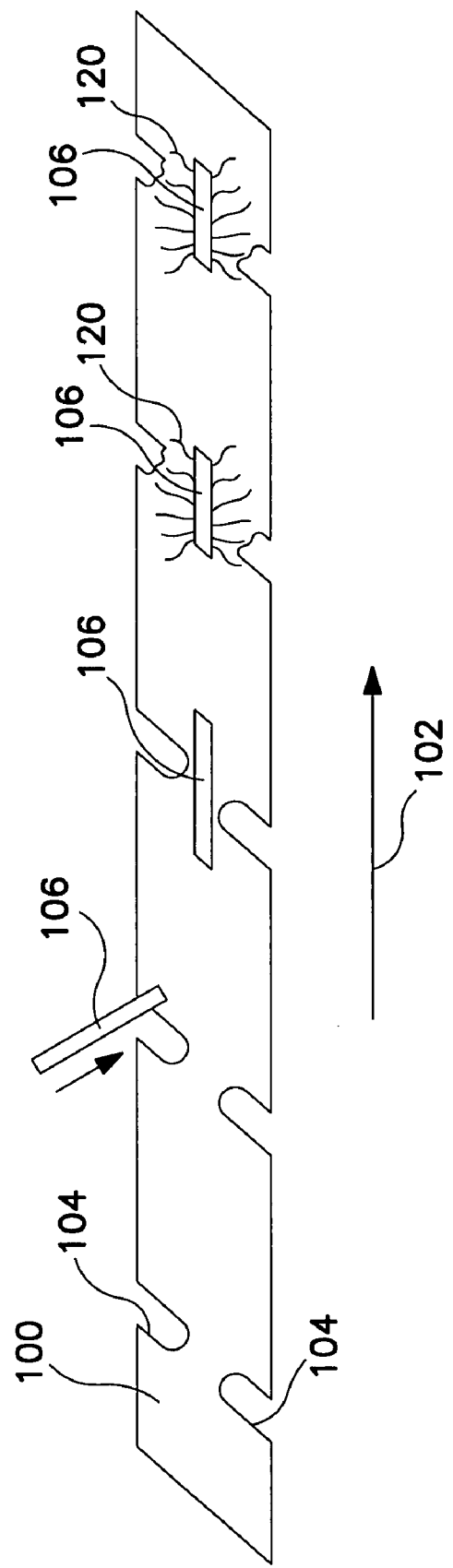
FIG. 8 is a side view of a process for applying a strip to the web.
Figure 9:
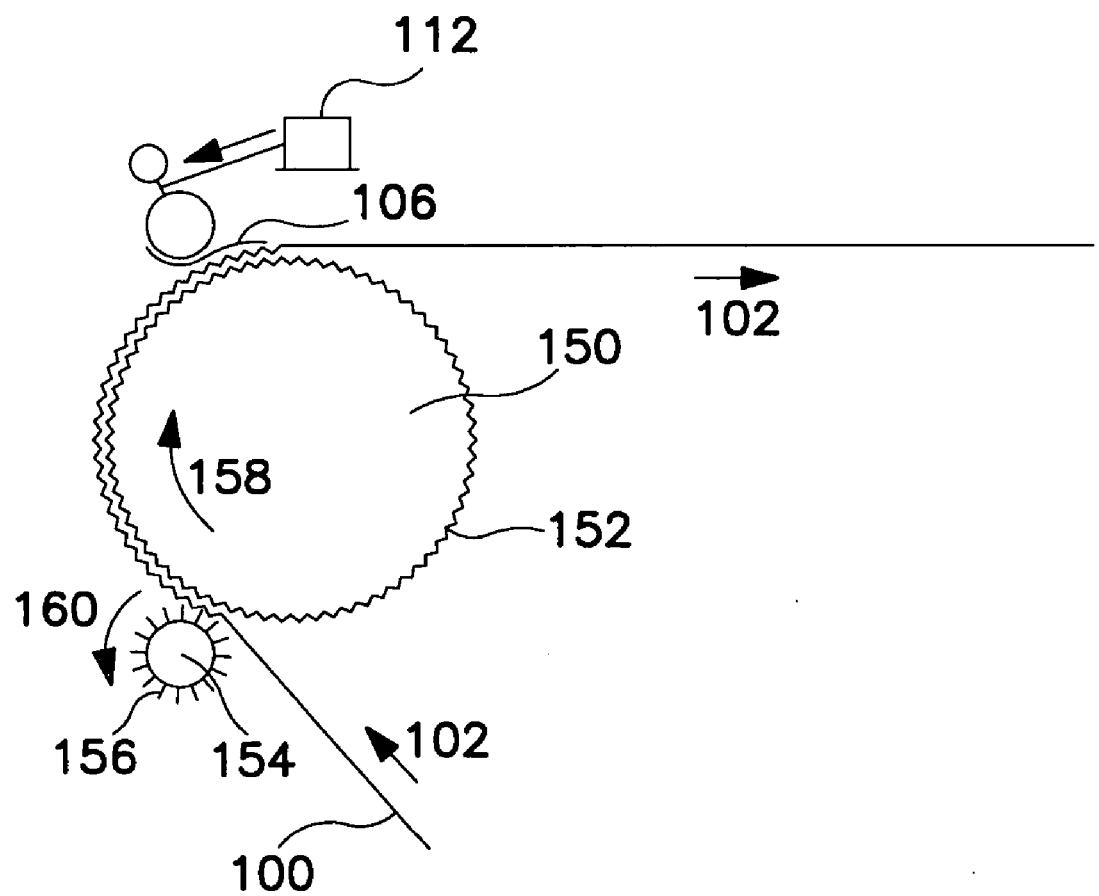
FIG. 9 is a side view of a corrugating drum for corrugating the web of FIG. 5.

Referring to FIG. 8, the strips 106, whether elastic or nonelastic, can be applied to the selected areas of the web 100 between the leg openings 104 by a cut-and-place module (not shown) as is commonly known in the art.

Next, the web 100 can be contracted elastically or inelastically by any suitable means. For example, if the strip 106 is an elastic capable of delayed retraction, the web 100 can be contracted by activating the strip 106 to restore the elasticity by time, temperature, radiation or other appropriate energy. If the strip 106 is a heat shrinkable material, the web 100 can be contracted inelastically by activating the heat shrinkable material by applying heat or other appropriate energy.

In particular embodiments, the strips 106 may be applied to the web 100 after contraction or pregathering of the web 100. In the machine direction, the web 100 can be pregathered by corrugating in the selected areas between the leg openings 104 by using a corrugating drum 150 (FIG. 9) in preparation for attachment of strip 106. Corrugating drums like corrugating drum 150 are known and are described, for example, in previously mentioned U.S. Pat. No. 4,397,704 issued Aug. 9, 1983 to Frick. Alternatively, a drum with discontinuous grooves that correlate with the location of strips 106 can be used. The web 100 travels around the drum 150 in the direction of arrow 158. Pressing roll 154 has teeth 156. The web 100 is pushed down into the grooves 152 by the teeth 156, thereby corrugating the web 100. Drum 150 and pressing roller 154 move in the direction of arrows 158 and 160, respectively.

Next, the strips 106 can be applied to the corrugated web 100 by a conventional cut-and-place applicator 112 or other appropriate apparatus. Strips 106 can be attached to the web 100 using adhesive, thermal or ultrasonic bonding, or other means known in the art. Use of a corrugating drum or other device to pregather the web 100 permits the use of an unstretched elastic or of a non-elastic, non-retractive material such as a film or nonwoven material with properties similar to the web 100. Alternatively, the strip 106 may include any of the previously described materials. The strips 106 maintain the corrugation in the contracted area 120 (FIG. 6).

In the cross direction process (FIGS. 10-12), as in the machine direction process, strips 106 can be applied to the selected areas located between the leg openings 104. In the cross direction assembly process, strips may be applied on the web 100 in an orientation essentially parallel with the longitudinal axis 48, as shown in FIG. 10.

The application of strip 106 of elastic material can be accomplished by a variety of methods, such as by moving the distal edges of the web 100 closer together and allowing the center portion of the web to become looped using the same principles of the previously described looper drum, but with the strip 106 being applied in an orientation perpendicular to arrow 102, or by other methods as are known in the art. As with the previously described looper drum, the web 100 can be fully extended again after application of the strip 106 in order to fully adhere the strip 106 to the web 100. In alternative embodiments, the strips 106 can be applied to the web 100 by a process in which an elastic or inelastic piece of material is cut, rotated and placed onto the web 100, for example, as described in U.S. Pat. No. 5,716,478 issued 10 Feb. 1998 to Boothe et al., U.S. Pat. No. 5,759,340 issued 2 Jun. 1998 to Boothe et al. and U.S. Pat. No. 4,608,115 issued 26 Aug. 1986 to Schroth et al., all of which are herein incorporated by reference, or by any other means known in the art. Where the strip 106 is a heat contractible material or a material capable of delayed retraction, the strip can be applied to web 100 as the web travels in the direction of arrow 102 (FIG. 10) in a flat and unlooped state.

The web 100 can be contracted elastically or inelastically by any of the previously described methods. FIG. 11 shows the web 100 after the contraction of the strips 100. The contraction of the web 100 defines contracted area 120 in the selected areas between the leg openings 104. The contracted area 120, as described more fully below, becomes the crotch region 26 of the pant 10.

In particular embodiments, the strips 106 are applied to the web 100 after contraction or pregathering of the web 100. In the cross direction, the web 100 can be pregathered by corrugating in the selected areas between the leg openings 104 by using intermeshing grooved rollers 170 and 172 (FIG. 12) in preparation for attachment of strip 106. Intermeshing grooved rollers like 170 and 172 are known in the art and are described, for example, in U.S. Pat. No. 5,755,902 issued 26 May 1998 to Reynolds, herein incorporated by reference. Roller 170 includes grooves 174 only in the middle portion of the roll to correspond to the desired location of the contracted area 120 on the web. The web 100 travels through nip 176 formed by rolls 170 and 172 in the direction of arrow 102. Roller 172 has complementary grooves (not shown) designed to intermesh with grooves 174 of roller 170. The web 100 is pushed into the grooves 174 by the complementary grooves on roll 172 to provide the corrugation in the contracted area 120. Rolls 170 and 172 move in the direction of arrows 178 and 180, respectively. The corrugations are held in place by attaching strips 106 on top of the corrugations.

The strip 106 can be applied to the corrugated web 100 by a cut-and-place module, or similar technology, as is commonly known in the art and can be attached to the web using thermal, ultrasonic or adhesive bonding, or any other means known in the art. The strip 106 may include an inextensible material such as a film or nonwoven material with properties similar to web 100, or may include any of the previously described materials.

In either the machine direction process or the cross direction process, the web 100 can now be cut into individual pieces, each of which will form a garment shell 64. The cutting can be accomplished by, for example, pinch cutting, shear cutting, or any other means known in the art. As another alternative, the web 100 can be provided as separate pre-cut pieces each of which pre-cut separate pieces will eventually become a single garment shell 64, so that this cutting step could be skipped and the process could start with a pre-cut piece as the web 100. FIG. 3C shows the garment shell 64 prior to folding and formation of the side seams 54. As shown and as previously mentioned with respect to FIGS. 1, 2A, and 2B the garment shell 64 can include a front region 22, a back region 24, a crotch region 26, an inner surface 28, and an outer surface 30 (not shown), front waist edge 38, back waist edge 39, and waist elastic member 58. The garment shell 64 can also include strip 106. It is also contemplated that the garment shell 64 can be made upside-down, i.e., with the inner surface 28 facing downwardly (not shown). The garment shell 64 can then be folded and the side seams 54 formed by any conventional method known in the art to form the pant 10 (without an absorbent structure). It is contemplated that the step of contracting the web 100 can occur either before or after the step of cutting into individual garment shells 64, and also before or after the formation of the side seams 54.

In either the machine direction process or the cross direction process, in alternative embodiments, the strip 106 need not be a single strip of material. In particular embodiments, elastic strands or ribbons as are known in the art can be used instead of a single strip of material for strip 106. The elastic strands or ribbons can be straight or curved. Alternatively, the crotch region 26 may include one or more strips 106 longitudinally offset, or multiple strips 106 arranged in a segmented manner, either spaced apart longitudinally or spaced apart transversely. In certain embodiments, the strip may be, at most, one-third the length of the garment shell when the garment shell is in a laid-flat, fully extended, namely uncontracted, condition. In addition, in the embodiments in which the web is corrugated or otherwise gathered, it is contemplated that instead of attaching a strip 106, the corrugation or gathers in the contracted area 120 can be maintained by fusing or bonding the corrugations together in the selected areas between the leg openings 104. The corrugations can be bonded to themselves to hold them in place by adhesive, thermal, or pressure bonding, or by any other means known in the art.

In the machine direction process, the strip 106 need not be a separate piece of material applied to the web 100. Instead, the web 100 may include an integral elastic zone aligned along the machine direction center line, instead of strip 106, with the elastic zone active in only the crotch region. Elasticization of only the crotch region of the pant may be achieved by, for example, an elastic laminate structure in which the elastic is attached to the laminate using an intermittent adhesive. Intermittent adhesive application would allow the elastic to snap back from non-adhesive zones, which would be uncontracted as a result; contracted, adhesive-bearing zones can be located only in the crotch region of the garment. As an alternative, the elastic nature of certain regions may be inactivated by chopping or overbonding the elastic or other methods known in the art, for example, as described in U.S. Pat. No. 6,248,097 issued Jun. 19, 2001 to Beitz, herein incorporated by reference.

As an alternative, or in addition, to the strip 106, expandable material 68 may be applied to the crotch region 26, as described above. Also described above, expandable material 68 may be applied to the back region 24, either in combination with expandable material 68 in the crotch region 26 or with a contracted crotch region 26.

Referring to FIGS. 2A, 2B, 3A, and 3B in particular embodiments, an absorbent structure 60 is included in the pant 10. The absorbent structure 60 can be introduced into the pant 10 in any suitable manner known in the art. In particular embodiments, the absorbent structure 60 can be placed on top of the crotch region 26 on the inner surface 28 of the garment shell 64, either prior to formation of side seams 54 or after side seams 54 are made. It is also contemplated, however, that the absorbent structure 60 can be attached prior to contracting and/or cutting the web 100. Where the absorbent structure 60 is added to the pant 10 prior to formation of side seams 54, cut and place methods such as are known in the art may be used. Alternatively, for a closed pant (i.e., side seams already formed), the absorbent structure 60 may be inserted into the pant such as by the method described in the PCT Publication WO 02/52967 by Rabe, et al., or by other means as may be known in the art. The absorbent structure 60 can be attached to the garment shell 64 at the front waist edge 38 and back waist edge 39, or at some point below the front waist edge 38 and back waist edge 39 on the front region 22 and back region 24. Additionally or alternatively, the absorbent structure 60 can be attached in the crotch region 26. The attachment can be accomplished by ultrasonic or adhesive bonding, or any other suitable method known in the art. As shown in FIGS. 2A and 2B, attachment to the front and back regions 22 and 24 provides for a loose fit of shell 64 in the crotch region 26, while the absorbent structure 60 is still held close to the body.

In particular embodiments, the absorbent structure 60 is stretchable or elasticizable in order to provide the desired close to the body fit for the absorbent structure 60 while the garment shell 64 hangs loosely. Alternatively, a suspension system for the absorbent structure may be required to provide a loose fit for the garment shell 64, such as described in U.S. Pat. No. 6,168,585 issued Jan. 2, 2001 to Cesco-Cancian, herein incorporated by reference.

The garment shell 64 with the absorbent structure 60 can then be folded and the side seams 54 formed by any conventional method known in the art to form the pant 10, as shown in FIGS. 2A and 2B. After folding the garment shell 64 and forming the side seams 54 (with or without an absorbent structure 60), if a temporarily inhibited elastic or latent elastic is used as the waist elastic 58, it may need to be activated to restore the elasticity. Alternatively, the elastics may be activated prior to seaming.

The various components of the pant can be connected together by any means known to those skilled in the art such as, for example, adhesive, thermal and/or ultrasonic bonds, pressure bonds and also sewing and other methods used in durable garment manufacturing. Most of the components may be connected using ultrasonic bonding for improved manufacturing efficiency and reduced raw material costs. For example, in particular embodiments, the side seams 54 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A pant made from a web, the pant comprising:
  a garment shell, the garment shell including a front region, a back region, a crotch region positioned between the front and back regions, a front waist edge, a back waist edge, side seams connecting the front region to the back region, two leg openings, and hanging legs, at least a portion of each of the front region, the back region, and the hanging legs comprising portions of the web;
  wherein the crotch region comprises an expandable material, at least a portion of the expandable material being set in an expanded configuration relative to the front region.

2. The pant of claim 1, wherein the front region, the back region, and the crotch region together comprise a single integral web of the expandable material.

3. The pant of claim 1, wherein the expandable material is attached to the front region and the back region of the garment shell.

4. The pant of claim 1, wherein the expandable material is attached to transversely opposed edges of the web in the crotch region.

5. The pant of claim 1, wherein the expandable material comprises a stretch-and-set material.

6. The pant of claim 1 wherein the expandable material comprises a necked material.

7. The pant of claim 1, wherein the expandable material comprises a corrugated material.

8. The pant of claim 1, further comprising an absorbent structure attached to the garment shell in at least one of the front region, the back region, and the crotch region.

9. A pant made from a web, the pant comprising:
  a garment shell, the garment shell including a front region, a back region, a crotch region positioned between the front and back regions, a front waist edge, a back waist edge, side seams connecting the front region to the back region, two leg openings and hanging legs, at least a portion of each of the front region, the back region, and the hanging legs comprising portions of the web;
  wherein the back region comprises an expandable material, at least a portion of the expandable material being set in an expanded configuration relative to the front region.

10. The pant of claim 9, wherein the front region, the back region, and the crotch region together comprise a single integral web of the expandable material.

11. The pant of claim 9, wherein the expandable material is attached to the web in the back region of the garment shell.

12. The pant of claim 11, wherein the crotch region comprises an expandable material attached to the garment shell.

13. The pant of claim 9, comprising a contracted crotch region.

14. The pant of claim 9, wherein at least a portion of the crotch region is stabilized.

15. The pant of claim 9, further comprising an absorbent structure attached to the garment shell in at least one of the front region, the back region, and the crotch region.

16. A method of making a pant having side seams and hanging legs, comprising:
  providing a web having a crotch region positioned between a front region and a back region;
  defining a leg opening along each of two transversely opposed edges of the web in the crotch region;
  providing an expandable material in the crotch region;
  setting at least a portion of expandable material in the crotch region in an expanded configuration relative to the front region; and
  attaching the front region and the back region together to form the side seams.

17. The method of claim 16, wherein the front region, back region, and the crotch region together comprise a single integral web of the expandable material.

18. The method of claim 16, comprising attaching the expandable material to the front region and the back region to form at least a portion of the crotch region.

19. The method of claim 16, comprising attaching the expandable material to transversely opposed edges of the web in the crotch region.

20. The method of claim 16, comprising expanding at least a portion of the expandable material in the crotch region.

21. The pant of claim 16, further comprising stabilizing at least a portion of the crotch region.

22. The method of claim 16, further comprising attaching an absorbent structure to the web in at least one of the front region, the back region, and the crotch region.

23. The method of claim 16 wherein the pant is made using a machine direction assembly.

24. The method of claim 16 wherein the pant is made using a cross direction assembly.

25. A method of making a pant having side seams and hanging legs, comprising:
  providing a web having a crotch region positioned between a front region and a back region;
  defining a leg opening along each of two transversely opposed edges of the web in the crotch region;
  providing an expandable material in the back region;
  setting at least a portion of the expandable material in back region in an expanded configuration relative to the front region; and
  attaching the front region and the back region together to form the side seams.

26. The method of claim 25, wherein the front region, the back region, and the crotch region together comprise a single integral web of the expandable material.

27. The method of claim 26, comprising expanding the expandable material in at least a portion of the crotch region.

28. The method of claim 27, comprising attaching the expandable material to the web in the back region.

29. The method of claim 28, comprising attaching an expandable material to the crotch region.

30. The method of claim 25, comprising expanding at least a portion of the expandable material in the back region.

31. The method of claim 25, further comprising contracting the web in the crotch region.

32. The method of claim 25, further comprising stabilizing at least a portion of the web in the crotch region.

33. The method of claim 25, further comprising attaching an absorbent structure to the web in at least one of the front region, the back region, and the crotch region.

34. The pant of claim 1, wherein the expandable material in the crotch region is set in an expanded configuration relative to the back region.

* * * * *

UNITED STATES PATENT AND TRADEMARK OFFICE
CERTIFICATE OF CORRECTION

| | | |
|---|---|---|
| PATENT NO. | : 8,361,049 B2 | Page 1 of 1 |
| APPLICATION NO. | : 10/954989 | |
| DATED | : January 29, 2013 | |
| INVENTOR(S) | : Coenen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1325 days.

Signed and Sealed this
Sixteenth Day of December, 2014

Michelle K. Lee
*Deputy Director of the United States Patent and Trademark Office*